(12) United States Patent
Hagihara

(10) Patent No.: US 12,270,641 B2
(45) Date of Patent: *Apr. 8, 2025

(54) MOTION DETECTION MEMBER

(71) Applicant: LINTEC CORPORATION, Tokyo (JP)

(72) Inventor: Yoshiaki Hagihara, Tokyo (JP)

(73) Assignee: LINTEC CORPORATION, Tokyo (JP)

( * ) Notice: Subject to any disclaimer, the term of this patent is extended or adjusted under 35 U.S.C. 154(b) by 196 days.

This patent is subject to a terminal disclaimer.

(21) Appl. No.: 17/911,588

(22) PCT Filed: Feb. 17, 2021

(86) PCT No.: PCT/JP2021/005998
§ 371 (c)(1),
(2) Date: Sep. 14, 2022

(87) PCT Pub. No.: WO2021/192748
PCT Pub. Date: Sep. 30, 2021

(65) Prior Publication Data
US 2023/0148077 A1 May 11, 2023

(30) Foreign Application Priority Data
Mar. 24, 2020 (JP) .................. 2020-053218

(51) Int. Cl.
*G01R 27/08* (2006.01)
*G01B 7/16* (2006.01)
*G06F 3/01* (2006.01)

(52) U.S. Cl.
CPC .............. *G01B 7/18* (2013.01); *G06F 3/014* (2013.01)

(58) Field of Classification Search
CPC ......... G01B 7/18; A41D 19/0027; A61B 5/11; A61B 5/6806; G06F 3/014; G06F 3/017; G06K 19/025; G06K 19/027
See application file for complete search history.

(56) References Cited

U.S. PATENT DOCUMENTS 12,007,355 B2 * 6/2024 Chou ..................... H05K 1/167
2017/0215495 A1 * 8/2017 Okumiya ................. G01B 7/16
(Continued)

FOREIGN PATENT DOCUMENTS

| JP | 2016-130940 A | 7/2016 |
| JP | 2017-061770 A | 3/2017 |
| WO | 2018/037855 A1 | 3/2018 |

OTHER PUBLICATIONS

International Search Report issued in corresponding International Patent Application No. PCT/JP2021/005998, dated Apr. 27, 2021, with English translation.

*Primary Examiner* — Thang X Le
(74) *Attorney, Agent, or Firm* — Rimon P.C.

(57) ABSTRACT

The present disclosure provides a motion detection member for detecting motion of a wearing body, the motion detection member including: a wearable part that is to be worn on the wearing body, the wearable part including an expanding/contracting portion that is configured from an expandable/contractible fabric material that expands/contracts as a result of the motion of the wearing body; and a wiring electrode part including: a wiring part provided at at least a portion of the expanding/contracting portion of the wearable part, the wiring part including a first wiring part including a conductive linear body and a second wiring part including a conductive linear body; and an electrode part including a first electrode part electrically connected to the first wiring part and a second electrode part electrically connected to the second wiring part.

18 Claims, 16 Drawing Sheets

(56) References Cited

U.S. PATENT DOCUMENTS

2018/0085060 A1* 3/2018 Shoshani .............. A61B 5/6805
2018/0347081 A1 12/2018 Kurahashi et al.
2020/0413533 A1* 12/2020 Majidi ................... H05K 1/189
2021/0219895 A1* 7/2021 Currano ................. A61B 5/313
2021/0381140 A1* 12/2021 Kimoto .................... D04B 1/10

* cited by examiner

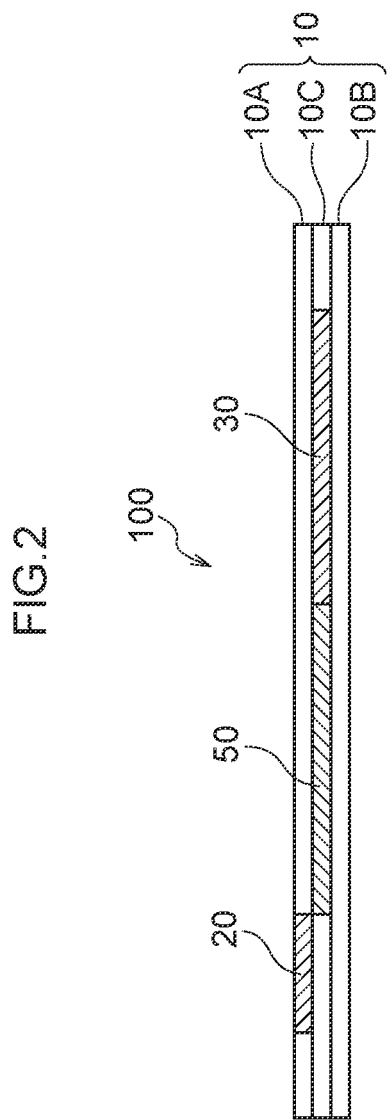

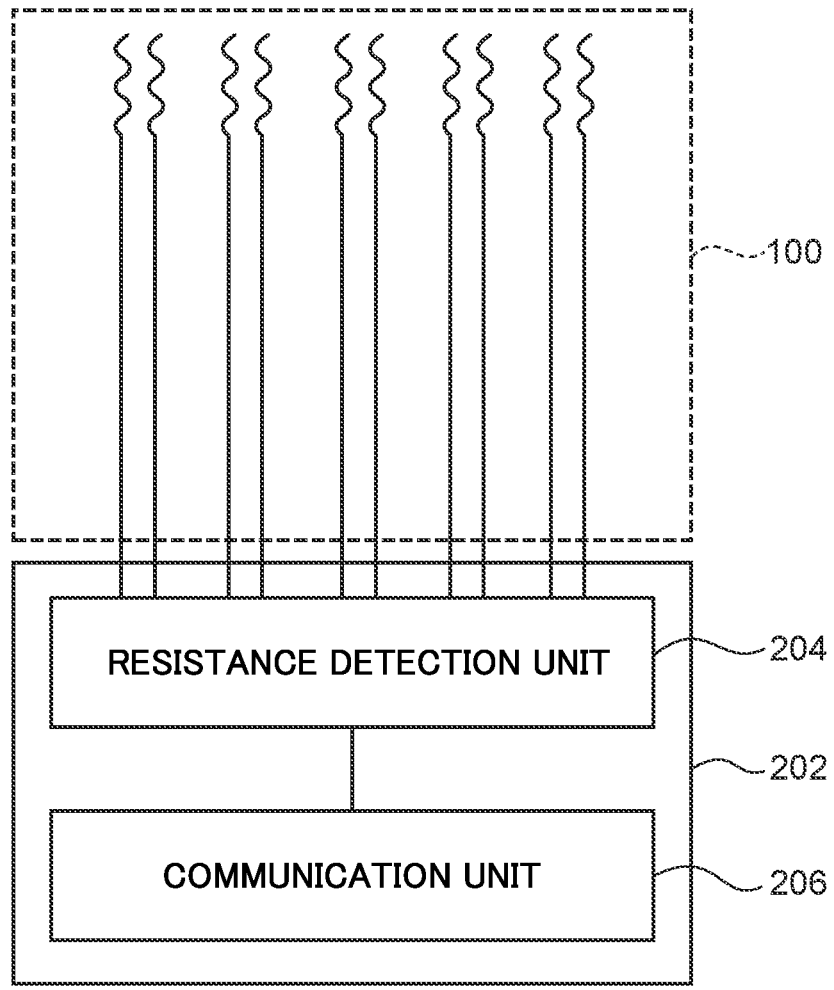

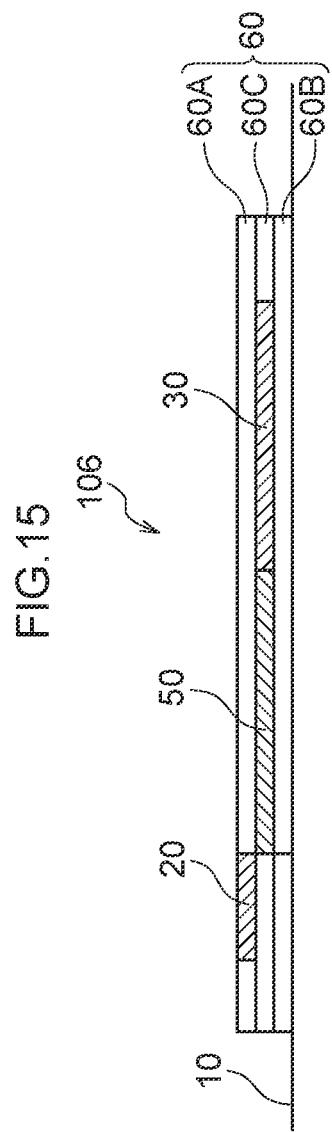

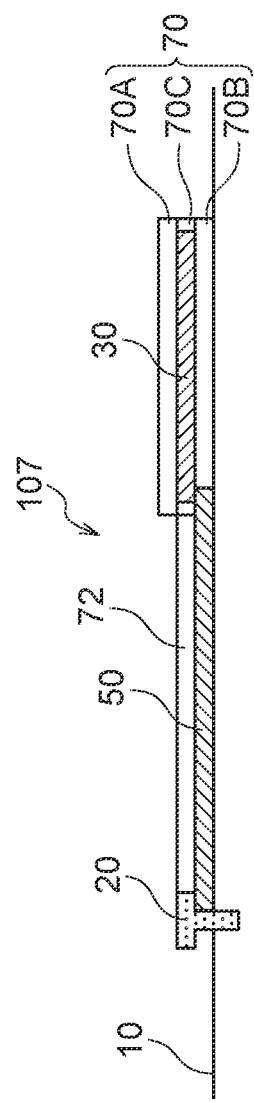

MOTION DETECTION MEMBER

CROSS REFERENCE TO RELATED APPLICATIONS

This application is the U.S. National Phase under 35 U.S.C. § 371 of International Application No. PCT/JP2021/005998 filed on Feb. 17, 2021, which claims the benefit of Japanese Application No. 2020-053218, filed on Mar. 24, 2020, the entire contents of each are hereby incorporated by reference.

TECHNICAL FIELD

The present disclosure relates to a motion detection member.

BACKGROUND ART

Conventionally, for example, a motion detection member for detecting the motion of human body parts (such as an elbow, knee, waist, or finger) and the like, is known.

For example, Japanese Patent Application Laid-Open (JP-A) No. 2016-130940 discloses "a glove-type input device to be worn on a hand to detect the motion or the shape of the hand of a user, the glove-type input device including a sensing device for detecting motion of a finger joint formed by using an expandable/contractible conductive ink at an outer side and/or an inner side of a glove configured from a material capable of expanding/contracting".

In addition, JP-A No. 2017-061770 discloses "a glove equipped with a strain sensor, the glove comprising: a glove main body that can be worn on a hand of a wearer; one or a plurality of sheet-shaped strain sensors that are provided at a joint-corresponding portion other than a surface at the palm side of the glove main body and that expand/contract so as to follow deformation of the glove main body; and an expandable/contractible wiring part that is provided integrally with the glove main body so as to deform and follow the deformation of the glove main body".

SUMMARY OF INVENTION

Technical Problem

However, in the motion detection member disclosed in JP-A No. 2016-130940, the detection part that detects the motion is formed using an expandable/contractible conductive ink. Therefore, durability is low.

Meanwhile, in the motion detection member disclosed in JP-A No. 2017-061770, the detection part that detects the motion includes a resin film (a film of a resin such as a silicone rubber or a urethane) as a base material. Therefore, the portion having the detection part may make a user feel uncomfortable, when wearing the motion detection member, due to the presence of the base material.

Thus, there is a demand for a motion detection member having a novel structure that is highly durable and comfortable to wear.

Therefore, an object of the present disclosure is to provide a motion detection member that is highly durable and comfortable to wear.

Solution to Problem

The foregoing problem is solved by the following means.
<1> A motion detection member for detecting motion of a wearing body, the motion detection member comprising:
a wearable part that is to be worn on the wearing body, the wearable part including an expanding/contracting portion that is configured from an expandable/contractible fabric material that expands/contracts as a result of the motion of the wearing body; and
a wiring electrode part including: a wiring part provided at at least a portion of the expanding/contracting portion of the wearable part, the wiring part including a first wiring part including a conductive linear body and a second wiring part including a conductive linear body; and an electrode part including a first electrode part electrically connected to the first wiring part and a second electrode part electrically connected to the second wiring part,
wherein, when the expanding/contracting portion of the wearable part, at which the wiring part is provided, expands/contracts as a result of the motion of the wearing body, a contact state between the first wiring part and the second wiring part changes, so that a resistance value between the first electrode part and the second electrode part changes.
<2> The motion detection member according to <1>, wherein:
the first wiring part and the second wiring part are separately provided;
in a case in which the first wiring part and the second wiring part are provided so that at least a portion of the first wiring part and at least a portion of the second wiring part are in contact with each other before expansion of the expanding/contracting portion of the wearable part, at which the wiring part is provided, when the expanding/contracting portion of the wearable part, at which the wiring part is provided, expands as a result of the motion of the wearing body, the first wiring part and the second wiring part move apart from each other; and
in a case in which the first wiring part and the second wiring part are provided so as to be apart from each other before expansion of the expanding/contracting portion of the wearable part, at which the wiring part is provided, when the expanding/contracting portion of the wearable part, at which the wiring part is provided, expands as a result of the motion of the wearing body, at least a portion of the first wiring part and at least a portion of the second wiring part come into contact with each other.
<3> The motion detection member according to <1> or <2>, wherein:
the first wiring part and the second wiring part are separately provided;
in a case in which the first wiring part and the second wiring part are provided so that at least a portion of the first wiring part and at least a portion of the second wiring part are in contact with each other before expansion of the expanding/contracting portion of the wearable part, at which the wiring part is provided, when the expanding/contracting portion of the wearable part, at which the wiring part is provided, expands as a result of the motion of the wearing body, a contact region between the first wiring part and the second wiring part gradually decreases, and in a case in which the first wiring part and the second wiring part are provided so as to be apart from each other before expansion of the expanding/contracting portion of the wearable part, at which the wiring part is provided, when the expanding/contracting portion of the wearable part, at which the wiring part is provided, expands as a result of the motion of the wearing body, the contact region between the first wiring part and the second wiring part gradually increases.

<4> The motion detection member according to <1>, wherein:

the first wiring part and the second wiring part are integrally provided; and when the expanding/contracting portion of the wearable part, at which the wiring part is provided, expands as a result of the motion of the wearing body, a conduction path of the first wiring part and the second wiring part lengthens.

<5> The motion detection member according to any one of <1> to <4>, having an expansion rate range such that, when the expanding/contracting portion of the wearable part, at which the wiring part is provided, is expanded to a maximum expansion rate, the resistance value between the first electrode part and the second electrode part changes by two times or more or by ½ or less within a range of an expansion rate change of 5%.

<6> The motion detection member according to any one of <1> to <5>, wherein the resistance value between the first electrode part and the second electrode part gradually changes according to an expansion rate of the expanding/contracting portion of the wearable part, at which the wiring part is provided.

<7> The motion detection member according to any one of <1> to <6>, wherein, when the expanding/contracting portion of the wearable part, at which the wiring part is provided, expands, a state between the first electrode part and the second electrode part shifts from a conduction state to a non-conduction state or from a non-conduction state to a conduction state.

<8> The motion detection member according to any one of <1> to <7>, wherein a portion of the conductive linear body in at least one of the first electrode part or the second electrode part is bound by a yarn of the expandable/contractible fabric material of the expanding/contracting portion of the wearable part.

<9> The motion detection member according to <8>, wherein the conductive linear body in at least one of the first electrode part or the second electrode part is woven into, knitted into, or embroidered onto the expandable/contractible fabric material of the expanding/contracting portion of the wearable part.

<10> The motion detection member according to any one of <1> to <9>, wherein a portion of the conductive linear body in at least one of the first wiring part or the second wiring part is bound by a yarn of the expandable/contractible fabric material of the expanding/contracting portion of the wearable part.

<11> The motion detection member according to <10>, wherein the conductive linear body in at least one of the first wiring part or the second wiring part is woven into, knitted into, or embroidered onto the expandable/contractible fabric material of the expanding/contracting portion of the wearable part.

<12> The motion detection member according to any one of <1> to <11>, wherein at least one of the first wiring part or the second wiring part is provided inside the expandable/contractible fabric material of the expanding/contracting portion of the wearable part.

<13> The motion detection member according to any one of <1> to <12>, wherein the conductive linear body included in at least one of the first electrode part, the second electrode part, the first wiring part, or the second wiring part is a conductive linear body that includes a carbon nanotube yarn.

<14> The motion detection member according to any one of <1> to <13>, wherein the wearable part is a glove-shaped wearable part that is to be worn on a hand of a human body serving as the wearing body.

<15> The motion detection member according to <14>, wherein the expanding/contracting portion, at which the wiring part is provided, faces at least one of a proximal interphalangeal joint or a metacarpophalangeal joint of a finger of the hand.

<16> The motion detection member according to any one of <1> to <13>, wherein the wearable part is a cylindrical, sheet-shaped, or belt-shaped wearable part.

<17> The motion detection member according to <16>, wherein the cylindrical, sheet-shaped, or belt-shape wearable part is a wearable part that is to be worn on a moving part of a human body serving as the wearing body.

<18> The motion detection member according to any one of <1> to <17>, wherein the expanding/contracting portion of the wearable part, at which the wiring part is provided, is provided at a surface of the wearable part.

Advantageous Effects of Invention

According to the present disclosure, it is possible to provide a motion detection member that is highly durable and comfortable to wear.

BRIEF DESCRIPTION OF DRAWINGS

FIG. 2 is a schematic cross-sectional view illustrating a motion detection member according to the present embodiment.

FIG. 4 is a block diagram illustrating the motion detection member according to the present embodiment.

FIG. 15 is a schematic cross-sectional view illustrating a wiring electrode part of a sixth modification.

FIG. 16 is a schematic cross-sectional view illustrating a wiring electrode part of a seventh modification.

DESCRIPTION OF EMBODIMENTS

Figure 1:
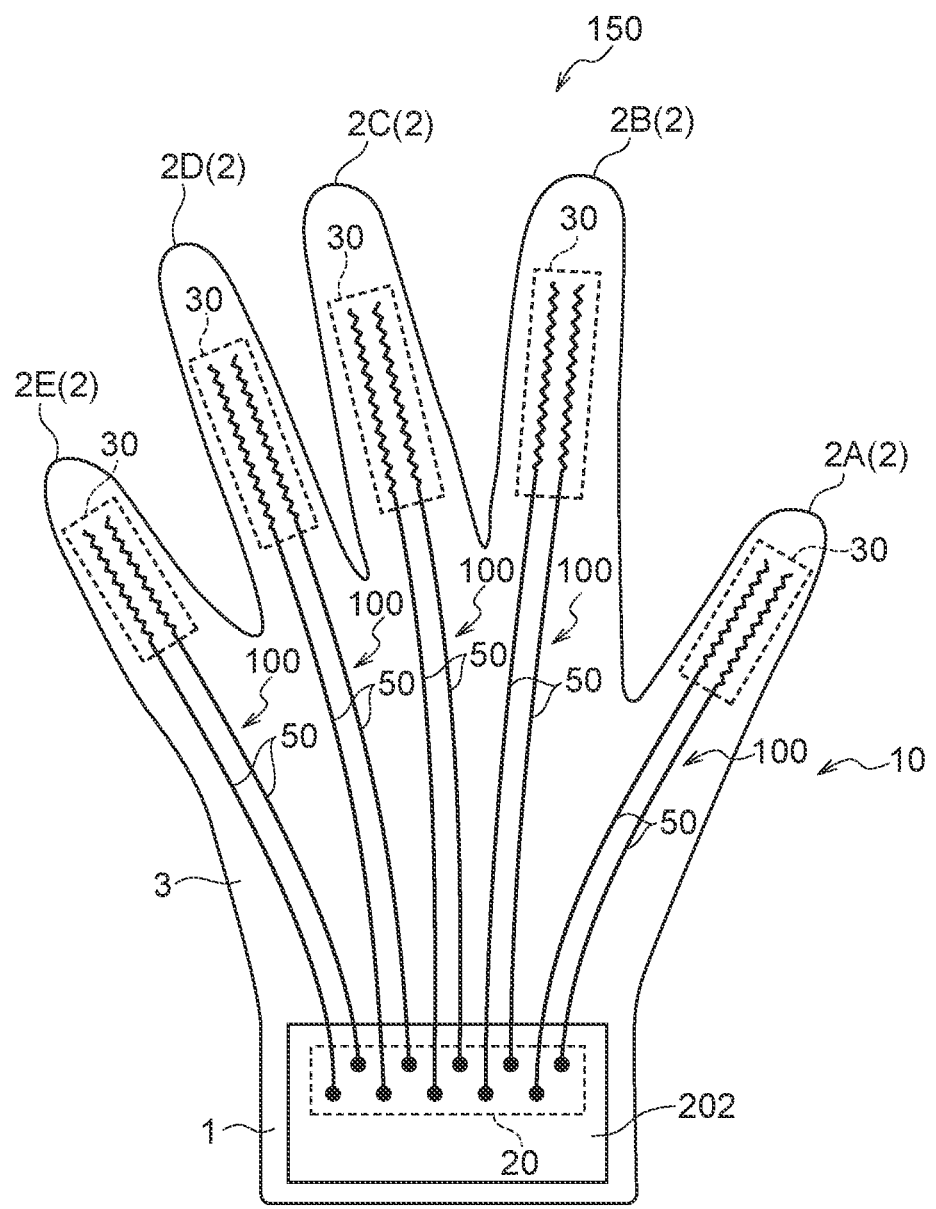
FIG. 1 is a schematic plan view illustrating a motion detection member according to the present embodiment.

Hereinafter, an exemplary embodiment of the present disclosure will be described in detail.

Note that, in the present specification, members having substantially the same functions are assigned the same reference signs throughout the drawings, and redundant descriptions may be omitted.

A numerical range using "to" signifies a numerical range in which the numerical values indicated before and after "to" are included as a minimum value and a maximum value, respectively.

In a numerical range described in stages, an upper limit value or a lower limit value described in one numerical range may be replaced with an upper limit value or a lower limit value of another numerical range described in stages.

The motion detection member according to the present embodiment is a member for detecting the motion of a wearing body.

The motion detection member according to the present embodiment includes:

a wearable part that is to be worn on the wearing body, the wearable part including an expanding/contracting portion that is configured from an expandable/contractible fabric material that expands/contracts as a result of the motion of the wearing body; and a wiring electrode part including: a wiring part provided at at least a portion of the expanding/contracting portion of the wearable part, the wiring part including a first wiring part including a conductive linear body and a second wiring part including a conductive linear body, and an electrode part including a first electrode part electrically connected to the first wiring part and a second electrode part electrically connected to the second wiring part, wherein, when the expanding/contracting portion of the wearable part, at which the wiring part is provided, expands/contracts as a result of the motion of the wearing body, a contact state between the first wiring part and the second wiring part changes, so that a resistance value between the first electrode part and the second electrode part changes.

In the motion detection member according to the present embodiment, when the expanding/contracting portion expands/contracts (that is, expands and contracts) as a result of motion of the wearing body, a contact state between the first wiring part and the second wiring part changes, so that a resistance value between the first electrode part and the second electrode part changes. By detecting the change in the resistance value, it is possible to detect the motion of the wearing body.

Further, in the motion detection member according to the present embodiment, the wiring electrode part for detecting motion is configured from a conductive linear body. Therefore, durability is also high.

In addition, a wiring part configured from a conductive linear body is provided at an expanding/contracting portion of the wearable part configured from an expandable/contractible fabric material. Therefore, discomfort is not readily felt when the motion detection member is worn on the wearing body, and the wearing feeling is excellent.

Further, the glove-type input device, the glove equipped with a strain sensor, and the like, of JP-A No. 2016-130940 require calibration in a state where a hand is open and a state where the hand is closed, and if the glove is continuously used, a sensor position is shifted, and there is a possibility of detection accuracy being reduced. In contrast, the motion detection member according to the present embodiment does not require calibration, can be used immediately after wearing, and has a wide permissible range of positional deviation.

Here, in the present specification, "the resistance value between the first electrode part and the second electrode part changes" indicates that 1) the resistance value increases or decreases while the state between the first electrode part and the second electrode part is a conductive state, or that 2) the state between the first electrode part and the second electrode part changes from a conductive state to a non-conductive state or from a non-conductive state to a conductive state. Note that the change in the resistance value does not include a change in the resistance value due to damage of the electrode part, the wiring part, or the junction between the electrode part and the wiring part.

The phrase "at least a portion of the first wiring part and at least a portion of the second wiring part are in contact with each other" may also include an embodiment in which, in a case in which another wiring part other than the first wiring part or the second wiring part (for example, a third wiring part) is included, at least a portion of the first wiring part and at least a portion of the second wiring part are in contact with each other via the other wiring part.

"The wiring part is provided at the expanding/contracting portion" indicates that "the wiring part is provided at the surface of an expandable/contractible fabric material" or "the wiring part is provided inside the expandable/contractible fabric material".

Further. "the wiring part is provided at the surface of the expandable/contractible fabric material" indicates that the wiring part (that is, the conductive linear body) is provided at a fabric material layer that constitutes the front or back surface of the expandable/contractible fabric material (which may also be a fabric material layer partially constituting the front or back surface). In other words, "the wiring part is provided at the surface of the expandable/contractible fabric material" indicates that the electrode part or the wiring part (that is, the conductive linear body) is provided in a state where at least a portion of the conductive linear body constituting the wiring part is exposed from the expandable/contractible fabric material.

Meanwhile, "the wiring part is provided inside the expandable/contractible fabric material" indicates that the wiring part (that is, the conductive linear body) is provided at the inner layer of the expandable/contractible fabric material, for example, in the fabric material layer serving as the inner layer of the expandable/contractible fabric material or between the fabric material layers.

"The wearable part includes an expanding/contracting portion configured from an expandable/contractible fabric material" encompasses both an embodiment in which a position corresponding to the expanding/contracting portion of the wearable part is configured from an expandable/contractible fabric material, and a wiring part is provided at the expandable/contractible fabric material, and an embodiment in which an expandable/contractible fabric material having a wiring part is separately bonded to the surface at a position corresponding to the expanding/contracting portion of the wearable part. Note that examples of the method of providing the expanding/contracting portion include bonding using an adhesive, attachment by sewing, and the like.

That is, the motion detection member includes, for example, both an embodiment in which a wiring part is provided at a position corresponding to the expanding/contracting portion of the wearable part that is configured from a fabric material or the like (such as a glove or a wristband), and an embodiment in which an expandable/contractible fabric material having a wiring part is separately bonded to the surface at a position corresponding to the expanding/contracting portion of a conventional wearable part (such as a glove or a wristband) configured from a known material such as a fabric material, a resin, paper, or leather.

Hereinafter, an example of the motion detection member according to the present embodiment will be described with reference to the drawings.

A motion detection member 150 according to the present embodiment is a glove-shaped member as illustrated in FIG. 1.

Specifically, the motion detection member 150 includes, for example, a glove-shaped wearable part 10 (an example of a wearable part), a wiring electrode part 100, and a communication module 202.

(Glove-Shaped Wearable Part)

The glove-shaped wearable part 10 is a glove-shaped wearable part that is to be worn on a hand of a human body serving as a wearing body.

The glove-shaped wearable part 10 includes a wrist part 1 to be worn on a wrist of a human body, a finger part 2 to be worn on a finger of the human body, and a body part 3 connecting the wrist part 1 and the finger part 2.

Note that the wrist part 1, a connecting part connecting the finger part 2 and the body part 3 (a portion corresponding to the metacarpophalangeal joint), and the finger part 2 (a portion corresponding to the distal interphalangeal joint and the proximal interphalangeal joint) corresponds to an example of the "expanding/contracting portion that expands/contracts as a result of motion of the wearing body".

Here, a portion of the finger part 2 facing the dorsal side of the proximal interphalangeal joint corresponds to an example of the "expanding/contracting portion of the wearable part, at which the wiring part is provided".

Here, the glove-shaped wearable part 10 includes, for example, five finger parts 2 corresponding to respective fingers. Specifically, the glove-shaped wearable part 10 has, as the finger parts 2, for example, a thumb part 2A that is to be worn on the thumb, an index finger part 2B that is to be worn on the index finger, a middle finger part 2C that is to be worn on the middle finger, a ring finger part 2D that is to be worn on the ring finger, and a little finger part 2E that is to be worn on the little finger.

However, the configuration of the finger part 2 is not limited to the configuration. The glove-shaped wearable part 10 may include, as the finger part 2, for example, two portions, namely, a thumb part that is to be worn on the thumb, and a finger part that is to be worn on the index finger, the middle finger, the ring finger, and the little finger.

The glove-shaped wearable part 10 is configured, for example, from triple (three layers of) fabric material layers, namely, a front surface fabric material layer 10A constituting a front surface, a back surface fabric material layer 10B constituting a back surface, and an intermediate fabric material layer 10C provided between the front surface fabric material layer 10A and the back surface fabric material layer 10B.

The glove-shaped wearable part 10 may be configured, for example, from one (single) fabric material layer, or from double (two) or quadruple (four) fabric material layers or more instead of the triple fabric material layers.

Note that multi-layer wearable part configured from two or more fabric material layers may be manufactured by, for example, a method of manufacturing respective fabric material layers and then sewing them together, or the multi-layer glove-shaped wearable part 10 may be collectively manufactured by a weaving or knitting machine.

The glove-shaped wearable part 10 is configured from an expandable/contractible fabric material, for example. In this regard, it is possible to configure the glove-shaped wearable part 10 from a soft fabric material, and to configure at least a portion of the finger part 2 facing the dorsal side of the proximal interphalangeal joint (an example of the expanding/contracting portion of the wearable part, at which the wiring part is provided) from an expandable/contractible fabric material.

Typical examples of the expandable/contractible fabric material are woven or knitted fabrics. The glove-shaped wearable part 10 may also be a nonwoven fabric.

Examples of woven or knitted fabrics include woven fabrics such as plain weave, twill weave, satin weave, and well-known weave applications; and knitted fabrics such as weft knitting, warp knitting, lace knitting, and well-known knitting applications.

The yarn (linear body) constituting the expandable/contractible fabric material is an insulating yarn. The insulating yarn refers to a yarn having a line resistance of $1.0 \times 10^6$ Ω/cm or more. The line resistance of the insulating yarn is a line resistance measured using the same method as for the line resistance of the conductive linear body described subsequently.

As the expandable/contractible fabric material, a woven or knitted fabric using an elastic yarn is preferably applied.

Examples of the elastic yarn include a covered yarn (single covered yarn or double covered yarn) for which an inelastic yarn is wound in a coil shape around an outer periphery of an elastic yarn, a core spun yarn for which an elastic yarn and an inelastic yarn are spun and twisted, an air-interlaced covered yarn for which an inelastic yarn is wound around an outer periphery of an elastic yarn using a pneumatic nozzle, and a twisted yarn for which an elastic yarn and an inelastic yarn are twisted.

Examples of the elastic yarn include yarns of fibers exhibiting so-called rubber-like elasticity, such as polyurethane elastic fibers, polyester elastic fibers, and polyamide elastic fibers.

Examples of the inelastic yarn include yarns of synthetic fibers (polyester fiber, polyamide fiber, acrylic fiber, polypropylene fiber, and rayon fiber) and natural fibers (fibers such as cotton, silk, hemp, and wool).

(Wiring Electrode Part)

A wiring electrode part 100 includes an electrode part 20, a wiring part 30, and a wiring part 50.

The electrode part 20 includes a first electrode part 20A and a second electrode part 20B, and is electrically connected to the communication module 202.

The wiring part 30 (hereinafter, referred to as the "detection wiring part 30") has a first wiring part 30A and a second wiring part 30B, and in the wiring part 30, a contact state between the first wiring part 30A and the second wiring part 30B changes when a portion of the finger part 2 facing a dorsal side of a proximal interphalangeal joint of a finger expands/contracts (hereinafter also referred to as "when the expanding/contracting portion of the finger part 2 expands/contracts") as a result of bending of the proximal interphalangeal joint of the finger (an example of motion of a wearing body).

The wiring part 50 has a first wiring part 50A and a second wiring part 50B, and is a connection wiring part (hereinafter referred to as the "connection wiring part 50") for electrically connecting the electrode part 20 and the wiring part 30.

Note that the connection wiring part 50 is a wiring part that is provided if necessary, and the electrode part 20 and the detection wiring part 30 may be directly connected.

—Electrode Part—

In the electrode part 20, the first electrode part 20A and the second electrode part 20B are each provided, for example, at the dorsal side of the wrist part 1 of the glove-shaped wearable part 10. However, the arrangement position of the electrodes is not particularly limited, and may be, for example, the palm side of the wrist part 1 of the glove-shaped wearable part 10 or the palm side of the body part 3 of the glove-shaped wearable part 10.

Note that three or more electrode parts 20 may be provided depending on the purpose. Only one electrode part 20 may also be provided.

For example, one electrode part may be a common electrode, and two or more wiring parts 50 may be connected to one electrode part. Examples of the present embodiment include an embodiment in which one of the two wiring parts 50 connected to the detection wiring part 30 disposed on the ring finger part 2D and one of the two wiring parts 50 connected to the detection wiring part 30 disposed on the little finger part 2E are connected to one electrode part serving as a common electrode.

For example, as illustrated in FIG. 2, the electrode part 20 is provided at the front surface fabric material layer 10A of the glove-shaped wearable part 10. That is, the electrode part 20 is provided at the surface of the glove-shaped wearable part 10.

Note that the electrode part 20 may be provided at the intermediate fabric material layer 10C of the glove-shaped wearable part 10. That is, the electrode part 20 may be provided inside the glove-shaped wearable part 10. This is because, even when the electrode part 20 is provided inside the glove-shaped wearable part 10, a connection can be established using a pin-shaped electrode or the like.

—Detection Wiring Part—

The detection wiring part 30 is provided at a portion of the finger part 2 (all parts, the thumb part 2A, index finger part 2B, middle finger part 2C, ring finger part 2D, and little finger part 2E) facing the dorsal side of the proximal interphalangeal joint of the finger.

However, the arrangement position of the detection wiring part 30 is not limited to that of the foregoing embodiment, and may be as per the following embodiments, depending on the purpose:

An embodiment in which the detection wiring part 30 is provided at a portion of the finger part 2 facing the dorsal side of the proximal interphalangeal joint and/or the dorsal side of the metacarpophalangeal joint of the finger.

An embodiment in which the detection wiring part 30 is provided at a portion of the finger part 2 facing the palm side of the proximal interphalangeal joint and/or the palm side of the metacarpophalangeal joint of the finger.

An embodiment in which a portion of the plurality of detection wiring parts 30 is provided at a position facing the portion of the finger part 2 facing the dorsal side of the finger, and the other portion is provided at a position facing the portion of the finger part 2 facing the palm side of the finger (for example, an embodiment in which a detection wiring part 30 is provided at a position facing the portion of the thumb part 2A facing the palm side of the thumb, and a detection wiring part 30 is provided at a position facing the portion of the index finger part 2B, the middle finger part 2C, the ring finger part 2D, and the little finger part 2E that face the dorsal side of the index finger part, the middle finger part, the ring finger part, and the little finger part).

An embodiment in which a detection wiring part 30 is provided at at least one of the thumb part 2A, the index finger part 2B, the middle finger part 2C, the ring finger part 2D, or the little finger part 2E.

In the detection wiring part 30, the first detection wiring part 30A is electrically connected to the first electrode part 20A. Further, the second detection wiring part 30B is electrically connected to the second electrode part 20B.

The first detection wiring part 30A and the second detection wiring part 30B are separately provided so as to be at least partially in contact with each other in a state before expansion of the expanding/contracting portion of the finger part 2.

However, in a case in which a portion of the detection wiring parts 30 is provided at a position facing the portion of the thumb part 2A facing the palm side of the finger (for example, in a case in which a detection wiring part 30 is provided at a position facing the portion of the thumb part 2A facing the palm side of the thumb, and a detection wiring part 30 is provided at a position facing the portion of the index finger part 2B, the middle finger part 2C, the ring finger part 2D, and the little finger part 2E facing the dorsal side of the index finger part, the middle finger part, the ring finger part, and the little finger part), in the detection wiring part 30 at a position facing the portion of the thumb part 2A facing the palm side of the thumb, the first detection wiring part 30A and the second detection wiring part 30B are separately provided so as to be apart from each other in a state before expansion of the expanding/contracting portion of the finger part 2.

Note that an embodiment in which the first detection wiring part 30A and the second detection wiring part 30B are separately provided so as to be apart from each other in a state before expansion of the expanding/contracting portion of the finger part 2, will be described in a first modification.

The first detection wiring part 30A extends, for example, along the longitudinal direction of the finger part 2. The first detection wiring part 30A has a wave-shaped part 32A that is obtained by providing a conductive linear body 40A2 in a wave shape.

The second detection wiring part 30B extends, for example, along the longitudinal direction of the finger part 2. The second detection wiring part 30B also has a wave-shaped part 32B that is obtained by providing a conductive linear body 40B2 in a wave shape.

In a state before expansion of the expanding/contracting portion of the finger part 2, the wave-shaped part 32A of the first detection wiring part 30A and the wave-shaped part 32B of the second detection wiring part 30B are in point contact or line contact with each other.

Note that both the first detection wiring part 30A and the second detection wiring part 30B may not have a wave-shaped part that is obtained by providing the conductive linear body 40A2 or the conductive linear body 40B2 in a wave shape, and may be configured to have only a linear part provided in a straight line. Further, the first detection wiring part 30A and the second detection wiring part 30B may both have a bent part that is obtained by bending the conductive linear body 40A2 or the conductive linear body 40B2.

The detection wiring part 30 is provided inside the glove-shaped wearable part 10. Specifically, for example, as illustrated in FIG. 2, the detection wiring part 30 is provided at the intermediate fabric material layer 10C, which is a fabric material layer (which may also be a fabric material layer partially serving as an inner layer) of the inner layer of the glove-shaped wearable part 10 that is configured from three fabric material layers, whereby the detection wiring part 30 can be provided inside the glove-shaped wearable part 10. Here, for example, the detection wiring part 30 may be provided between the fabric material layers of the glove-shaped wearable part 10, which is configured from two fabric material layers.

Note that the detection wiring part 30 may be provided at the surface of the glove-shaped wearable part 10. For example, the detection wiring part 30 may be provided at the front surface fabric material layer 10A or the back surface fabric material layer 10B of a glove-shaped wearable part 10 that is configured from three fabric material layers. However, the detection wiring part 30 is preferably provided inside the glove-shaped wearable part 10 from the viewpoint of insulation from the outside by the glove-shaped wearable part 10.

—Connection Wiring Part 50—

In the connection wiring part 50, the first connection wiring part 50A electrically connects the first electrode part 20A and the first wiring part 30A. The second connection wiring part 50B electrically connects the second electrode part 20B and the second wiring part 30B.

The connection wiring part 50 is provided at the body part 3 of the glove-shaped wearable part 10 facing the dorsal side of the hand.

However, the arrangement position of the connection wiring part 50 is not limited to the embodiment, and is set according to the arrangement positions of the electrode part 20 and the detection wiring part 30.

The connection wiring part 50 is provided inside the glove-shaped wearable part 10. Specifically, for example, as illustrated in FIG. 2, the connection wiring part 50 is provided at the intermediate fabric material layer 10C, which is a fabric material layer (which may also be a fabric material layer partially serving as an inner layer) of the inner layer of the glove-shaped wearable part 10 that is configured from three fabric material layers, whereby the connection wiring part 50 can be provided inside the glove-shaped wearable part 10. Here, for example, the connection wiring part 50 may be provided between the fabric material layers of the glove-shaped wearable part 10, which is configured from two fabric material layers.

Note that the connection wiring part 50 may be provided at the surface of the glove-shaped wearable part 10. For example, the connection wiring part 50 may be provided at the front surface fabric material layer 10A or the back surface fabric material layer 10B of the glove-shaped wearable part 10, which is configured from three fabric material layers.

However, the connection wiring part 50 is preferably provided inside the glove-shaped wearable part 10 from the viewpoint of insulation from the outside by the glove-shaped wearable part 10.

—Conductive Linear Body—

Each of the electrode part 20, the detection wiring part 30, and the connection wiring part 50 includes a conductive linear body 40. That is, the region where the conductive linear body 40 is disposed is used for the electrode part 20, the detection wiring part 30, and the connection wiring part 50.

Specifically, for example, the first electrode part 20A includes a conductive linear body 40A1.

The first connection wiring part 50A includes a conductive linear body 40A3 extending from the conductive linear body 40A1 of the first electrode part 20A.

The first detection wiring part 30A includes a conductive linear body 40A2 extending from the conductive linear body 40A3 of the first connection wiring part 50A.

That is, the first electrode part 20A and the first detection wiring part 30A are configured from at least the same one conductive linear body 40.

Here, for example, the second electrode part 20B includes a conductive linear body 40B1.

The second connection wiring part 50B includes a conductive linear body 40B3 extending from the conductive linear body 40B1 of the second electrode part 20B.

The second detection wiring part 30B includes a conductive linear body 40B2 extending from the conductive linear body 40B3 of the second connection wiring part 50B.

That is, the second electrode part 20B and the second detection wiring part 30B are configured from at least the same one conductive linear body 40.

The first electrode part 20A and the first detection wiring part 30A, and the second electrode part 20B and the second detection wiring part 30B, respectively, are configured from the same one conductive linear body 40, whereby a connection failure between the electrode part 20 and the detection wiring part 30 is suppressed.

Note that the same one conductive linear body 40 may also include a linear body in which end portions of conductive linear bodies 40 are connected to each other by knotting, twisting, or the like without using a connecting material (solder, conductive paste, or the like) or a connecting member (crimping, a connector, or the like) other than a linear body.

However, each of the electrode part 20, the detection wiring part 30, and the connection wiring part 50 may also include a plurality of conductive linear bodies 40. Here, the first electrode part 20A, the first detection wiring part 30A, and the first connection wiring part 50A, and the second electrode part 20B, the second detection wiring part 30B, and the second connection wiring part 50B, respectively, may not be configured from the same one conductive linear body 40.

For example, the ends of conductive linear bodies 40 of the first electrode part 20A, the first detection wiring part 30A, and the first connection wiring part 50A, and the ends of the second electrode part 20B, the second detection wiring part 30B, and the second connection wiring part 50B, respectively, may be connected to each other using a connecting material (solder, conductive paste, or the like) or a connecting member (crimping, a connector, or the like) other than a linear body.

In at least one of the electrode part 20, the detection wiring part 30, and the connection wiring part 50, for example, at least a portion of the conductive linear body 40 is bound by the yarn of the glove-shaped wearable part 10.

Such an embodiment is preferable from the viewpoint that the conductive linear body 40 functioning as a conductive material can also be used as a means for fixing to the glove-shaped wearable part 10 as the electrode part 20, the detection wiring part 30, and the connection wiring part 50.

The conductive linear body 40 bound to the glove-shaped wearable part 10 may be the same one conductive linear body 40 included in the electrode part 20, the detection wiring part 30, and the connection wiring part 50, or may be another conductive linear body 40 included in only one of the electrode part 20, the detection wiring part 30, and the connection wiring part 50.

In at least one of the electrode part 20, the detection wiring part 30, and the connection wiring part 50, the conductive linear body 40 may not be bound by the yarn of the glove-shaped wearable part 10.

For example, in a case in which at least one of the electrode part 20, the detection wiring part 30, and the connection wiring part 50 is fixed to the glove-shaped wearable part 10 using an adhesive, when at least one of the electrode part 20, the detection wiring part 30, and the connection wiring part 50 is sewn to the glove-shaped wearable part 10 by using an insulating yarn, at least one of the electrode part 20, the detection wiring part 30, and the connection wiring part 50 can be fixed to the glove-shaped wearable part 10 even when the conductive linear body 40 is not bound by the yarn of the glove-shaped wearable part 10.

For example, a rectangular region in which the conductive linear body 40 is repeatedly bent or curved at 180° is formed. This rectangular region is formed by binding a portion of the conductive linear body 40 to the yarn of the front surface fabric material layer 10A of the glove-shaped wearable part 10. Further, this rectangular region may be used as a planar electrode part 20.

Note that a region in which a conductive linear body 40 is arranged in a spiral shape may also be used as the electrode part 20. Here, an arbitrary planar shape (polygon, circle, or the like) in which the conductive linear body 40 is bent or curved may also be used as the electrode part 20.

Meanwhile, a region is formed in which the conductive linear body 40 is extended from the electrode part 20 in a linear shape, a wave shape, a bent shape, or a combination thereof. This region is formed by binding a portion of the conductive linear body 40 to the yarn of the intermediate fabric material layer 10C of the glove-shaped wearable part 10. This region may be used as the detection wiring part 30 and the connection wiring part 50.

Figure 5:
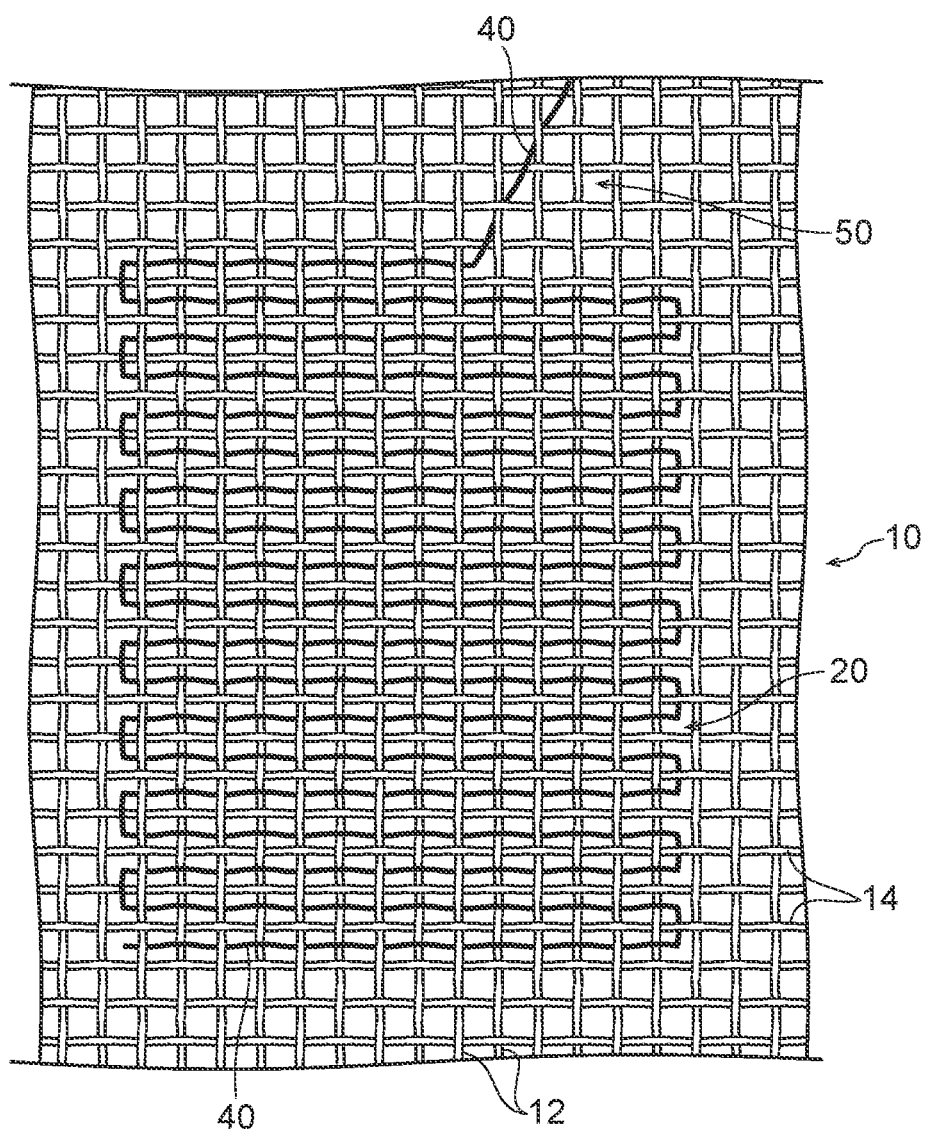
FIG. 5 is a schematic plan view illustrating an example in which a conductive linear body is woven into the motion detection member according to the present embodiment.

Specifically, in a case in which the glove-shaped wearable part 10 is a woven fabric, as illustrated in FIG. 5, the electrode part 20, the detection wiring part 30, and the connection wiring part 50 are preferably configured by weaving the conductive linear body 40 into a woven structure of a woven fabric that is woven with warps and wefts, from the viewpoint that the glove-shaped wearable part 10, the electrode part 20, the detection wiring part 30, and the connection wiring part 50 can be simultaneously formed when the glove-shaped wearable part 10 is formed by weaving, and from the viewpoint of improving the integrity of the glove-shaped wearable part 10, the electrode part 20, the detection wiring part 30, and the connection wiring part 50.

Figure 6:
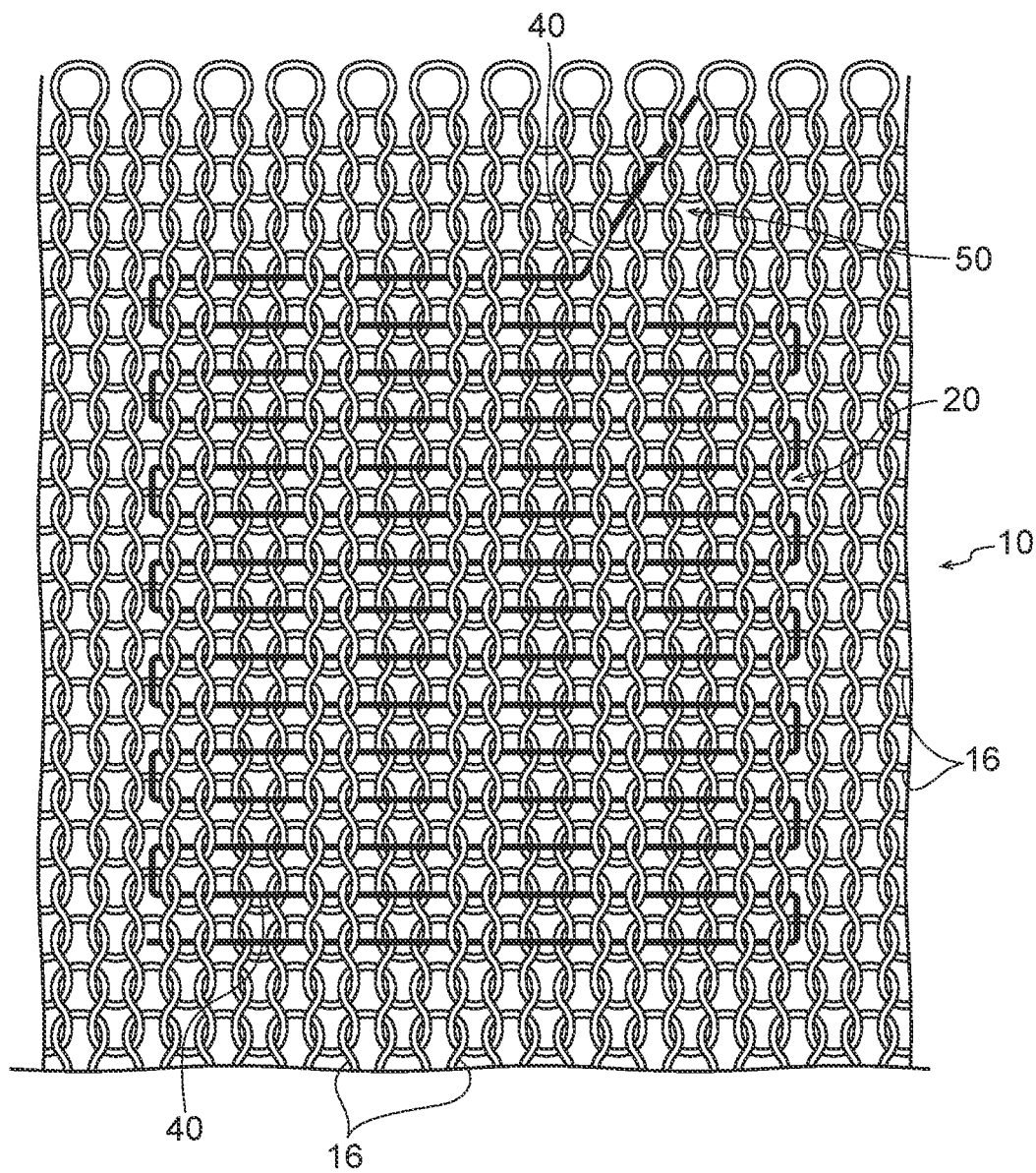
FIG. 6 is a schematic plan view illustrating an example in which a conductive linear body is knitted into the motion detection member according to the present embodiment.

In a case in which the glove-shaped wearable part 10 is a knitted fabric, as illustrated in FIG. 6, it is preferable that the electrode part 20, the detection wiring part 30, and the connection wiring part 50 are configured by knitting the conductive linear body 40 in the aforementioned shape into a knitted structure of the knitted fabric in which a loop-shaped yarn is knitted, from the viewpoint that the glove-shaped wearable part 10, the electrode part 20, the detection wiring part 30, and the connection wiring part 50 can be simultaneously formed when the glove-shaped wearable part 10 is formed by knitting, and from the viewpoint of improving the integrity of the glove-shaped wearable part 10, the electrode part 20, the detection wiring part 30, and the connection wiring part 50.

In the case of knitting the conductive linear body 40 into the knitted structure of the knitted fabric, for example, aligned knitting, plating knitting, inlay knitting, and the like can be adopted. FIG. 6 illustrates an example in which the conductive linear body 40 is knitted by adopting inlay knitting.

Figure 7:
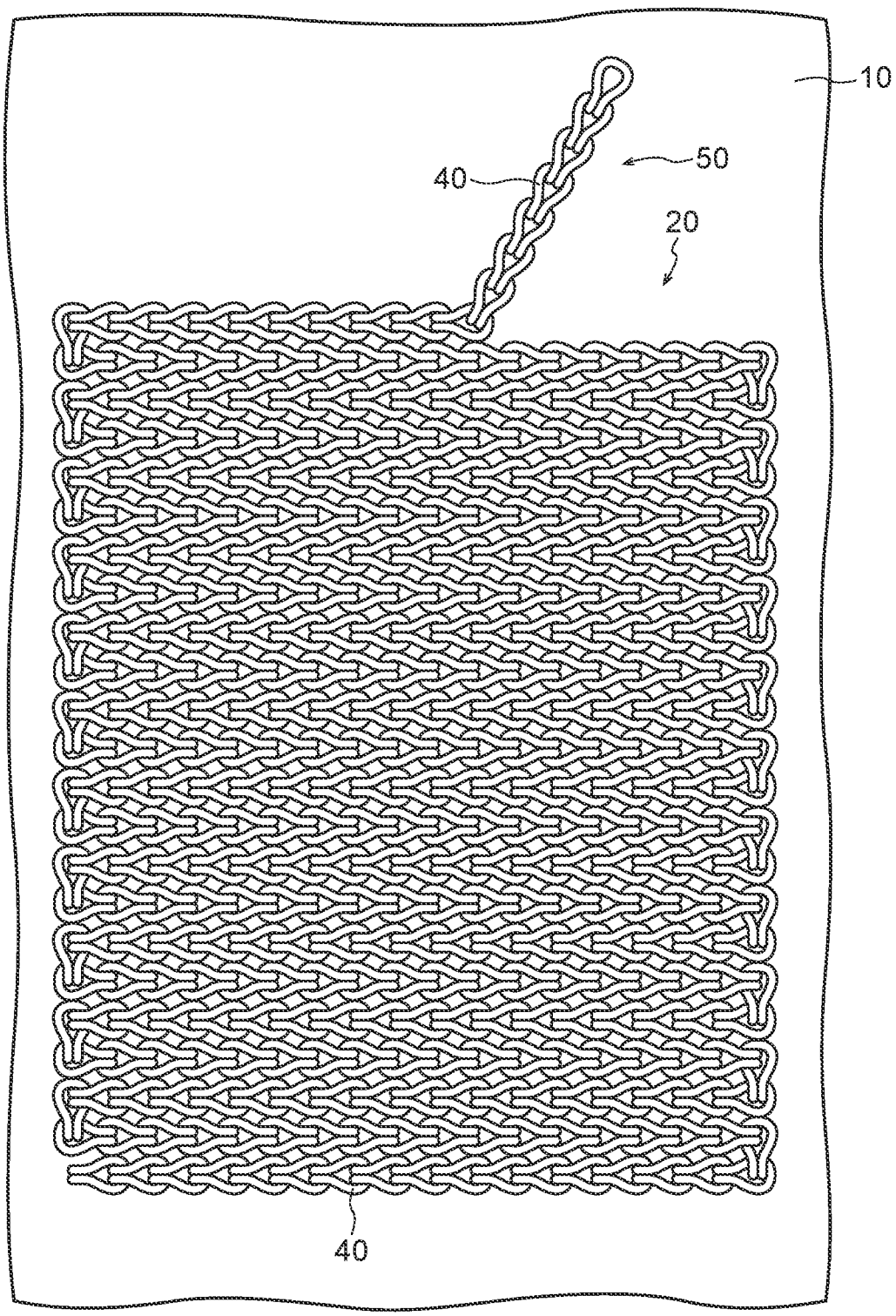
FIG. 7 is a schematic plan view illustrating an example in which a conductive linear body is embroidered onto the motion detection member according to the present embodiment.

Here, as illustrated in FIG. 7, it is preferable that the electrode part 20, the detection wiring part 30, and the connection wiring part 50 are configured by embroidering the conductive linear body 40 in the aforementioned shape with respect to the glove-shaped wearable part 10, from the viewpoint that the electrode part 20, the detection wiring part 30, and the connection wiring part 50 can also be fixed to the glove-shaped wearable part 10 at the same time when the electrode part 20, the detection wiring part 30, and the connection wiring part 50 are formed.

For example, a well-known stitch such as a running stitch, a coaching stitch, a back stitch, a chain stitch, and an outline stitch can be adopted as the embroidering method. FIG. 7 illustrates an example in which the conductive linear body 40 is embroidered using chain stitches.

Here, it is preferable that the electrode part 20, the detection wiring part 30, and the connection wiring part 50 are sewn and fixed to the glove-shaped wearable part 10 by the conductive linear body 40, from the viewpoint that the conductive linear body 40 constituting the electrode part 20, the conductive linear body 40 fixing the detection wiring part 30, and the conductive linear body 40 fixing the connection wiring part 50 can be made common.

For example, examples of embodiments in which the electrode part 20, the detection wiring part 30, and the connection wiring part 50 are sewn and fixed by the conductive linear body 40 include an embodiment in which: the electrode part 20, the detection wiring part 30, and the connection wiring part 50 are continuously formed from a woven fabric into which the conductive linear body 40 is woven or a knitted fabric into which the conductive linear body 40 is knitted; and the electrode part 20, the detection wiring part 30, and the connection wiring part 50 are sewn to the glove-shaped wearable part 10 by using the conductive linear body 40.

In FIG. 5, reference sign 12 denotes a warp constituting the glove-shaped wearable part 10 (woven fabric), and reference sign 14 denotes a weft constituting the glove-shaped wearable part 10 (woven fabric). In FIG. 6, reference sign 16 denotes a yarn that constitutes the glove-shaped wearable part 10 (woven fabric).

Note that, when the elastic yarn is adopted as the yarn constituting the glove-shaped wearable part 10, the conductive linear body 40 may be woven or knitted into the glove-shaped wearable part 10 while forming a woven or knitted fabric in a state where the elastic yarn is expanded.

(Conductive Linear Body)

The conductive linear body constituting the electrode part 20, the detection wiring part 30, and the connection wiring part 50 is not particularly limited as long as it has conductivity, and examples thereof include a linear body including a metal wire, and a linear body including a conductive yarn. The conductive linear body 40 may also be a linear body including a metal wire and a conductive yarn (a linear body obtained by twisting a metal wire and a conductive yarn, or the like).

Because both the linear body including the metal wire and the linear body including the conductive yarn have high electrical conductivity, when applied as the conductive linear body 40, the resistance of the electrode part 20, the detection wiring part 30, and the connection wiring part 50 can be easily reduced.

Examples of the metal wire include wires containing a metal such as copper, aluminum, tungsten, iron, molybdenum, nickel, titanium, silver, or gold, or an alloy (for example, steel such as stainless steel and carbon steel, or brass, phosphor bronze, zirconium copper alloy, beryllium copper, iron nickel, nichrome, nickel titanium, Kanthal. Hastelloy, rhenium tungsten, and the like) containing two or more kinds of metals. Further, the metal wire may be plated with tin, zinc, silver, nickel, chromium, a nickel-chromium alloy, solder, or the like, or may have a surface coated with a carbon material or a polymer (described subsequently).

Examples of the metal wire also include a metal wire coated with a carbon material When the metal wire is coated with a carbon material, metal corrosion is suppressed.

Examples of the carbon material covering the metal wire include amorphous carbon such as carbon black, activated carbon, hard carbon, soft carbon, mesoporous carbon, and carbon fiber; graphite; fullerene; graphene; carbon nanotubes, and the like.

Meanwhile, the linear body including the conductive yarn may be a linear body composed of one conductive yarn or a may be a linear body obtained by twisting a plurality of conductive yarns. Here, the conductive yarn and the insulating yarn may be twisted. The linear body including the conductive yarn has higher flexibility than the linear body including the metal wire, and has an advantage that disconnection due to weaving into, knitting into, or embroidering onto the glove-shaped wearable part 10, or sewing into the glove-shaped wearable part 10, does not readily occur.

Examples of the conductive yarn include, a yarn (hereinafter, a carbon nanotube yarn) that contains conductive fibers (metal fibers, carbon fibers, fibers of an ion-conductive polymer, and the like); a yarn containing conductive fine particles (carbon nanoparticles and the like); a yarn having a surface which is plated or vapor-deposited with a metal (copper, silver, nickel, and the like), and a yarn impregnated with a metal oxide.

Suitable examples of a linear body that includes a conductive yarn include, in particular, a linear body that includes a carbon nanotube yarn (hereinafter also referred to as the "carbon nanotube linear body").

The carbon nanotube linear body is obtained, for example, by drawing a carbon nanotube in a sheet shape from an end of a carbon nanotube forest (a growth body obtained by growing a plurality of carbon nanotubes on a substrate such that the carbon nanotubes are oriented in a direction perpendicular to the substrate, which may be referred to as an "array"), bundling the drawn carbon nanotube sheets, and then twisting a bundle of carbon nanotubes. In such a manufacturing method, when no twist is applied during twisting, a ribbon-shaped carbon nanotube linear body is obtained, and when a twist is applied, a yarn-shaped linear body is obtained. The ribbon-shaped carbon nanotube linear body is a linear body having no structure in which a set of a plurality of carbon nanotubes is twisted. In addition, a carbon nanotube linear body can also be obtained by spinning from a dispersion liquid of carbon nanotubes, or the like. The manufacturing of the carbon nanotube linear body by spinning can be carried out, for example, using the method disclosed in US Patent Publication No. 2013/0251619 (JP Laid-Open Application No. 2011-253140). From the viewpoint of obtaining uniformity of the diameter of the carbon nanotube linear body, it is desirable to use a yarn-shaped carbon nanotube linear body, and from the viewpoint of obtaining a carbon nanotube linear body of high purity, it is preferable to obtain a yarn-shaped carbon nanotube linear body by twisting a carbon nanotube sheet. The carbon nanotube linear body may be a linear body in which two or more carbon nanotube linear bodies are twisted with each other.

The carbon nanotube linear body may be a linear body (hereinafter also referred to as the "composite linear body") that includes a carbon nanotube and a conductive material other than a carbon nanotube, such as metal, a conductive polymer, or graphene. The composite linear body readily improves the conductivity of the linear body while maintaining the aforementioned characteristics of the carbon nanotube linear body.

Examples of linear bodies including carbon nanotubes and a metal that serve as the composite linear body include: (1) a composite linear body in which a single metal or a metal alloy is carried on the surface of a carbon-nanotube forest, sheet or bundle, or a twisted linear body by vapor deposition, ion plating, sputtering, wet plating, or the like, in the process of drawing carbon nanotubes in a sheet shape from the end of the carbon nanotube forest, bundling the drawn carbon nanotube sheets, and then obtaining a carbon nanotube linear body in which a bundle of carbon nanotubes is twisted; (2) a composite linear body obtained by twisting together a bundle of carbon nanotubes with: a linear body of a single metal, a linear body of a metal alloy, or a composite linear body, and (3) a composite linear body obtained by twisting together a carbon nanotube linear body or a composite linear body with: a linear body of a single metal, a linear body of a metal alloy, or a composite linear body. Note that, in the composite linear body of (2), when a bundle of carbon nanotubes is twisted, a metal may be carried on the carbon nanotubes as per the composite linear body of (1). Here, the composite linear body of (3) is a composite linear body obtained by knitting two linear bodies; however, as long as at least one linear body of a single metal, a linear body of a metal alloy, or a composite linear body is included, three or more carbon nanotube linear bodies, linear bodies of a single metal, linear bodies of a metal alloy, or composite linear bodies may be knitted together.

Examples of possible metals for the composite linear body include: simple metals such as gold, silver, copper, iron, aluminum, nickel, chromium, tin, and zinc, and alloys that include at least one of these simple metals (copper-nickel-phosphorus alloy, copper-iron-phosphorus-zinc alloy, and the like).

Among these conductive linear bodies 40, conductive linear bodies that include a carbon nanotube yarn (in particular, a conductive linear body including only a carbon nanotube yarn or a conductive linear body including a carbon nanotube yarn and a nonmetallic conductive material) are preferable.

For example, a yarn that has a metal (copper, silver, nickel, and the like) plated or vapor-deposited on its surface or a yarn impregnated with a metal oxide will likely be subject to cracks in the metal or metal oxide when expansion/contraction is repeated, and hence durability is low. In this regard, the carbon nanotube linear bodies have strong resistance to bending, and even when the expanding/contracting portion of the finger part 2 repeatedly expands/contracts, the resistance value of the wiring part hardly changes. The carbon nanotube linear bodies also have the advantage of exhibiting high corrosion resistance.

Here, the linear resistance of the conductive linear body 40 is preferably $5.0 \times 10^{-3}$ Ω/cm to $1.0 \times 10^{3}$ Ω/cm, and more preferably $1.0 \times 10^{-2}$ Ω/cm to $5.0 \times 10^{2}$ Ω/cm.

The line resistance of the conductive linear body 40 is measured as follows. First, a silver paste is applied to both ends of the conductive linear body 40, and the resistance of a portion between the silver pastes is measured to determine the resistance value (unit: Ω) of the conductive linear body 40. The resistance value thus obtained is then divided by the distance (cm) between the silver pastes to calculate the line resistance of the conductive linear body 40.

(Communication Module)

The communication module 202 is provided, for example, at the dorsal side of the wrist part 1 of the glove-shaped wearable part 10. However, the arrangement position of the communication module 202 is not particularly limited, and may be, for example, the palm side of the wrist part 1 of the glove-shaped wearable part 10 or the palm side of the body part of the glove-shaped wearable part 10.

The communication module 202 is electrically connected to the electrode part 20 via a connection terminal (not illustrated).

The communication module 202 is detachably provided on the glove-shaped wearable part 10 by a means such as a hook-and-loop fastener, for example. By taking out the communication module 202 from the glove-shaped wearable part 10, the motion detection member 150 can be washed without performing waterproofing on the communication module.

The communication module 202 has a resistance detection unit 204 and a communication unit 206, and note that the communication module 202 also has a power supply unit (not illustrated).

In the communication module 202, the resistance detection unit 204 detects the resistance value between the first electrode part 20A and the second electrode part 20B. The data of the detected resistance value is transmitted to an external device by the communication unit 206.

Note that the embodiment may be such that the motion detection member 150 according to the present embodiment transmits the data of the detected resistance value to the external device in a wired manner.

(Action of Motion Detection Member)

Figure 3A:
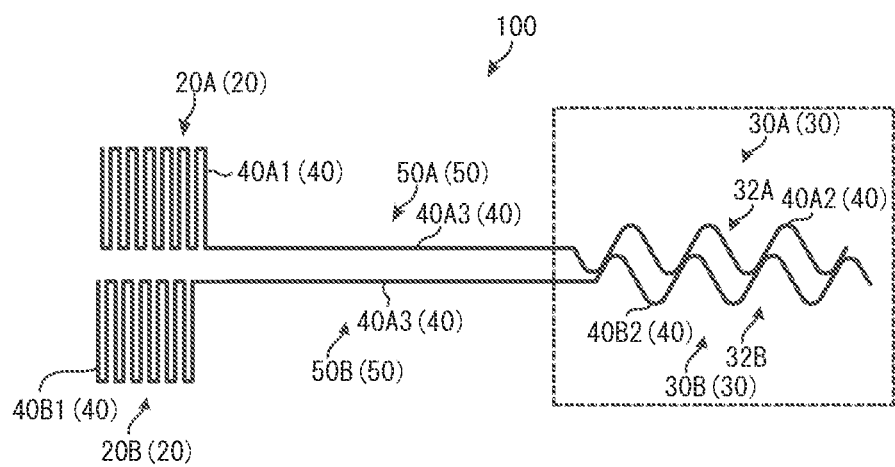
FIG. 3A is a schematic plan view illustrating an expanding/contracting portion (an example of an expanding/contracting portion of a wearable part, at which a wiring part is provided) of a motion detection member according to the present embodiment.

In the motion detection member 150 according to the present embodiment, at least respective portions (in the present embodiment, the wave-shaped parts 32A and 32B) of the first detection wiring part 30A and the second detection wiring part 30B are in contact with each other in a state before expansion of the expanding/contracting portion of the finger part 2 in the glove-shaped wearable part 10 (see FIG. 3A). Specifically, at least a portion of the conductive linear body 40A2 constituting the first detection wiring part 30A and at least a portion of the conductive linear body 40B2 constituting the second detection wiring part 30B are in contact with each other.

Figure 3B:
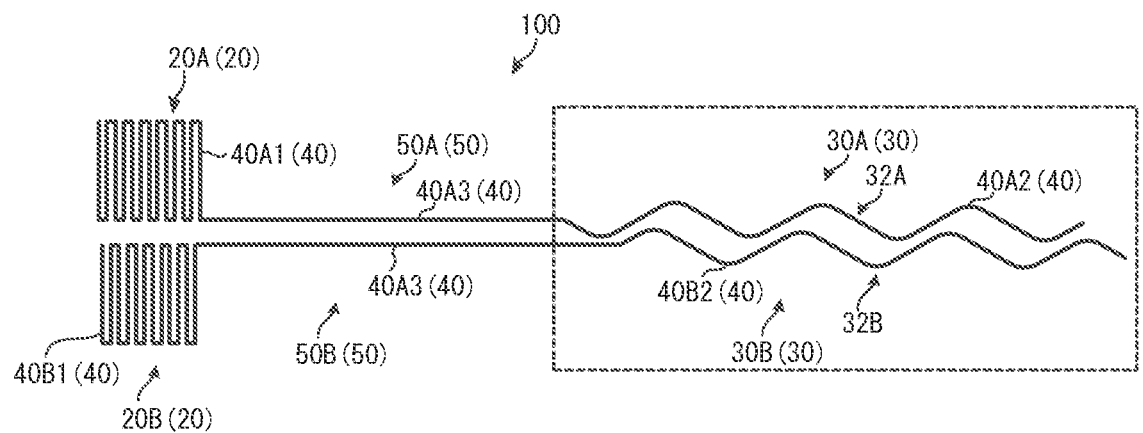
FIG. 3B is a schematic plan view illustrating an expanded state of an expanding/contracting portion (an example of the expanding/contracting portion of the wearable part, at which the wiring part is provided) of a finger part of the motion detection member according to the present embodiment.

However, when the expanding/contracting portion of the finger part 2 in the glove-shaped wearable part 10 expands as a result of bending of the finger of the hand (bending of the proximal interphalangeal joint), the first detection wiring part 30A and the second detection wiring part 30B move apart from each other at the moment when a certain expansion rate is reached (see FIG. 3B). Specifically, the conductive linear body 40A2 constituting the first detection wiring part 30A and the conductive linear body 40B2 constituting the second detection wiring part 30B move apart from each other.

More specifically, when the expanding/contracting portion of the finger part 2 expands, the period of the wave-shaped part 32A of the first detection wiring part 30A and the wave-shaped part 32B of the second detection wiring part 30B becomes long, and the amplitude thereof becomes small. As a result, the first detection wiring part 30A and the second detection wiring part 30B move apart from each other.

When the expanding/contracting portion of the finger part 2 expands as a result of this motion, the resistance value between the first electrode part 20A and the second electrode part 20B changes. That is, the resistance value increases. Specifically, the state between the first electrode part 20A and the second electrode part 20B shifts from a conduction state to a non-conduction state.

The motion of the finger (bending of the proximal interphalangeal joint of the finger) can then be detected by detecting the change in resistance value between the first electrode part 20A and the second electrode part 20B that accompanies the expansion.

However, when the bending of the finger of the hand (the bending of the proximal interphalangeal joint) is released and the expansion of the expanding/contracting portion of the finger part 2 is released (that is, when it contracts), at least a portion of the first detection wiring part 30A and at least a portion of the second detection wiring part 30B, which have been apart from each other, come into contact with each other at the moment when a certain expansion rate is reached (see FIG. 3A). That is, the resistance value is reduced. Specifically, the state between the first electrode part 20A and the second electrode part 20B shifts from a non-conduction state to a conduction state.

Thus, the motion of a finger (release of bending of the proximal interphalangeal joint of the finger) can be detected by detecting a change in the resistance value between the first electrode part 20A and the second electrode part 20B that accompanies the expansion and contraction.

Figure 8:
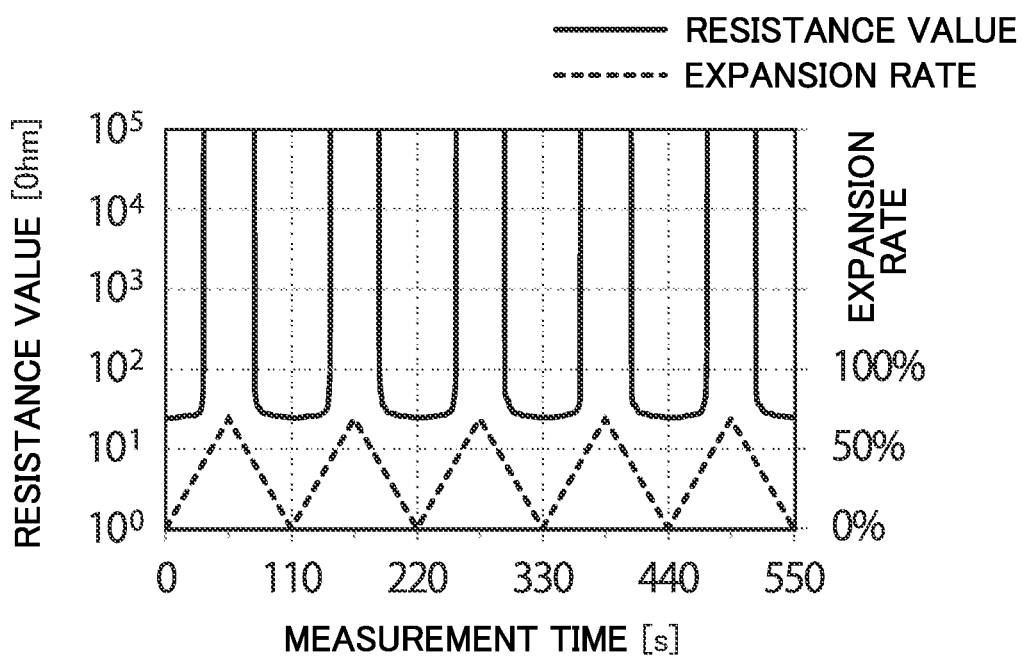
FIG. 8 is a diagram illustrating an example of a "relationship between a resistance value between a first electrode part and a second electrode part, and a measurement time, and a relationship between an expansion rate and the measurement time" in a case in which expansion and contraction of an expanding/contracting portion (an example of the expanding/contracting portion of the wearable part, at which the wiring part is provided) up to a maximum expansion rate are repeated five times.
Figure 9:
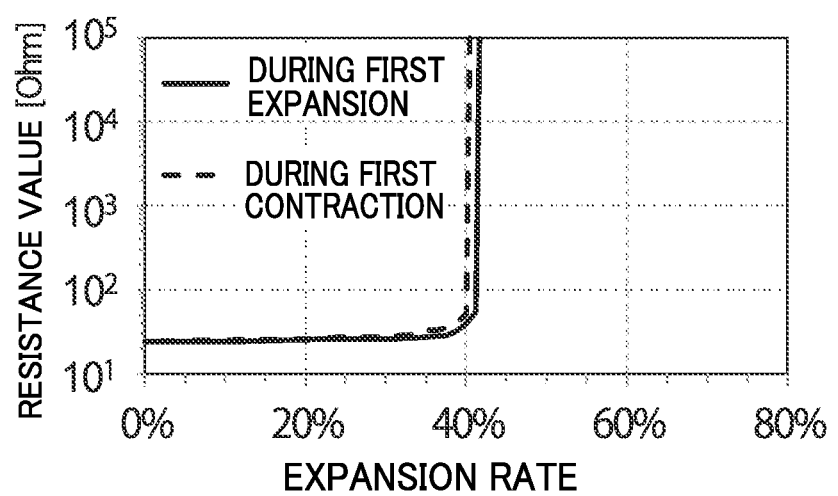
FIG. 9 is a diagram illustrating an example of "a relationship between a resistance value and an expansion rate between a first electrode part and a second electrode part" in a first expansion/contraction based on the results of FIG. 9.

Here, FIG. 8 illustrates an example of "the relationship between the resistance value between the first electrode part 20A and the second electrode part 20B, and the measurement time, and the relationship between the expansion rate and the measurement time" when a motion to expand the expanding/contracting portion of the finger part 2 to an expansion rate of 70% and then contract the expanding/contracting portion of the finger part 2 (that is, the expanding/contracting portion of the wearable part, at which the detection wiring part is provided), which has the maximum expansion rate (=about 80%), is repeated five times at an expansion speed of 1 mm/s. FIG. 9 illustrates an example of "the relationship between the resistance value between the first electrode part 20A and the second electrode part 20B, and the expansion rate" in the first expansion/contraction based on the measurement results of FIG. 8.

As illustrated in FIGS. 8 to 9, when the expanding/contracting portion (that is, the expanding/contracting portion of the wearable part, at which the detection wiring part is provided) of the finger part 2 expands/contracts, the resistance value between the first electrode part 20A and the second electrode part 20B changes with a certain expansion rate as a boundary. Specifically, the state between the first electrode part 20A and the second electrode part 20B shifts from a conduction state to a non-conduction state, and from a non-conduction state to a conduction state.

As illustrated in FIGS. 8 to 9, the motion detection member 150 can detect the motion of a finger (bending of the proximal interphalangeal joint of the finger and release thereof) by detecting a change in the resistance value between the first electrode part 20A and the second electrode part 20B that accompanies the expansion and contraction of the expanding/contracting portion of the finger part 2 (that is, the expanding/contracting portion of the wearable part, at which the detection wiring part is provided).

Note that, in the measurement results of the resistance value change illustrated in FIGS. 8 to 9, it is found that when the expansion rate is in the range of about 43.7%±5% on average, the resistance value increases during expansion, and the resistance value decreases during contraction.

(Uses for Motion Detection Member)

For example, because the motion detection member 150 according to the present embodiment can detect the motion of a finger, it can be used in an input device for displaying hand states (for example, rock, paper, scissors in a rock-paper-scissors game) or in an input device for operating games, or the like.

(Modification of Wiring Electrode Part)

In the case of the motion detection member 150 according to the present embodiment, the wiring electrode part is not limited to the configuration of the wiring electrode part 100 illustrated in FIG. 3, and may be modified or improved.

Hereinafter, a modification of the wiring electrode part in the motion detection member according to the present embodiment will be described.

Note that, in the following description, as long as the wiring electrode part is the same as in the member described in the foregoing embodiment, the wiring electrode part is assigned the same reference sign throughout the drawings, and a description thereof is omitted or simplified.

Further, in the following description, the connection wiring part will be omitted.

—First Modification—

Figure 10A:
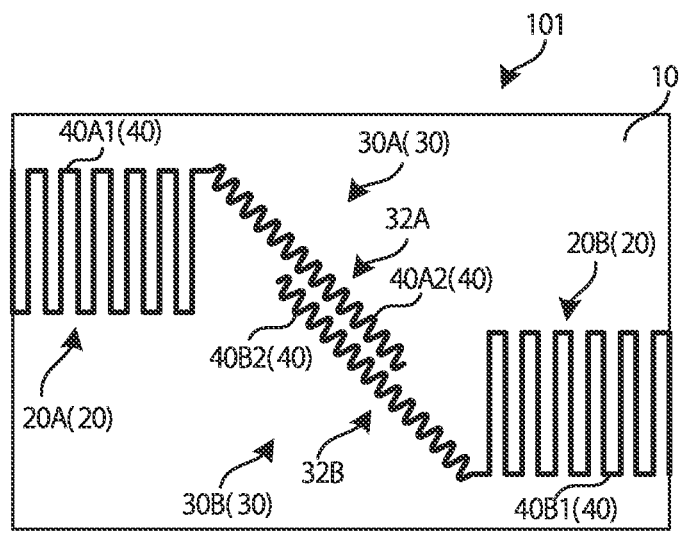
FIG. 10A is a schematic plan view illustrating a wiring electrode part of a first modification.

The wiring electrode part may be, for example, the wiring electrode part 101 illustrated in FIG. 10A.

Specifically, as illustrated in FIG. 10A, in the wiring electrode part 101, the first detection wiring part 30A and the second detection wiring part 30B are provided so as to be apart from each other in a state before expansion of the expanding/contracting portion (hereinafter, simply referred to as the "expanding/contracting portion of the wearable part") of the wearable part, at which the detection wiring part 30 is provided. Further, the wave-shaped part 32A of the first detection wiring part 30A and the wave-shaped part 32B of the second detection wiring part 30B face each other substantially in parallel and are provided so as to be apart from each other.

Figure 10B:
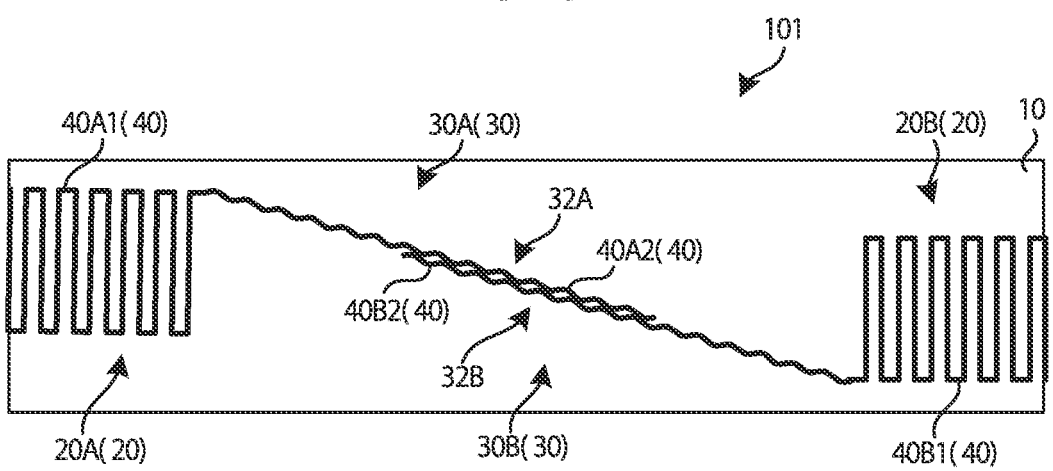
FIG. 10B is a schematic plan view illustrating an expanded state of the wiring electrode part of the first modification.

When the expanding/contracting portion of the wearable part expands as a result of the motion of the wearing body, at least a portion of the first detection wiring part 30A and at least a portion of the second detection wiring part 30B, which have been apart from each other, come into contact with each other at the moment when a certain expansion rate is reached (see FIG. 10B). Specifically, at least a portion of the conductive linear body 40A2 constituting the first detection wiring part 30A and at least a portion of the conductive linear body 40B2 constituting the second detection wiring part 30B come into contact with each other.

More specifically, when the expanding/contracting portion of the wearable part expands, the period of the wave-shaped part 32A of the first detection wiring part 30A and the wave-shaped part 32B of the second detection wiring part 30B becomes long, and the amplitude thereof becomes small, while contact is made therebetween.

When the expanding/contracting portion of the wearable part expands as a result of this motion, the resistance value between the first electrode part 20A and the second electrode part 20B changes. That is, the resistance value is reduced. Specifically, the state between the first electrode part 20A and the second electrode part 20B shifts from a non-conduction state to a conduction state.

The motion of the wearing body can then be detected by detecting the change in resistance value between the first electrode part 20A and the second electrode part 20B that accompanies the expansion.

However, when the expansion of the expanding/contracting portion of the wearable part is released (that is, when the expanding/contracting portion contracts) as a result of the motion of the wearing body, the first detection wiring part 30A and the second detection wiring part 30B, which have been in contact with each other, move apart from each other at the moment when a certain expansion rate is reached (see FIG. 10A). That is, the resistance value increases. Specifically, the state between the first electrode part 20A and the second electrode part 20B shifts from a conduction state to a non-conduction state.

Thus, the motion of the wearing body can be detected by detecting a change in resistance value between the first electrode part 20A and the second electrode part 20B that accompanies the contraction.

—Second Modification—

Figure 11A:
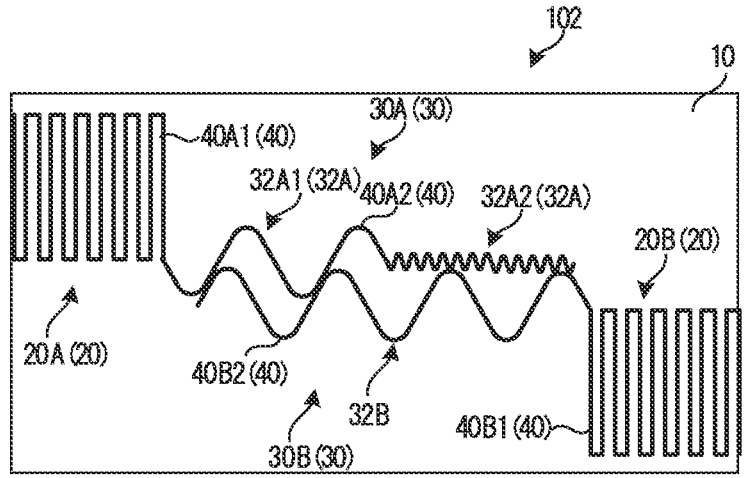
FIG. 11A is a schematic plan view illustrating a wiring electrode part of a second modification.

The wiring electrode part may be, for example, the wiring electrode part 102 illustrated in FIG. 11A.

Specifically, as illustrated in FIG. 11A, the wiring electrode part 102 includes, as the wave-shaped part 32A of the first detection wiring part 30A, a first wave-shaped part 32A1 and a second wave-shaped part 32A2 which has a different contact length with the wave-shaped part 32B of the second detection wiring part 30B than first wave-shaped part 32A1.

Further, the wiring electrode part 102 has, as the wave-shaped part 32A of the first detection wiring part 30A, a first wave-shaped part 32A 1 and a second wave-shaped part 32A2 which has a different period and/or amplitude than the first wave-shaped part 32A1.

Note that the present example represents an example in which the second wave-shaped part 32A2 has a shorter contact length with the wave-shaped part 32B of the second detection wiring part 30B than the first wave-shaped part 32A1. Here, an example is illustrated in which the second wave-shaped part 32A2 has a shorter period and a smaller amplitude than the first wave-shaped part 32A1.

When the expanding/contracting portion (hereinafter, simply referred to as the "expanding/contracting portion of the wearable part") of the wearable part, at which the detection wiring part 30 is provided, expands as a result of the motion of the wearing body, a portion of the first detection wiring part 30A and a portion of the second detection wiring part 30B, which have been in contact with each other, move apart from each other at the moment when a certain expansion rate is reached (see FIG. 11B). Specifically, the second wave-shaped part 32A2 of the first detection wiring part 30A and the wave-shaped part 32B of the second detection wiring part 30B move apart from each other.

Figure 11B:
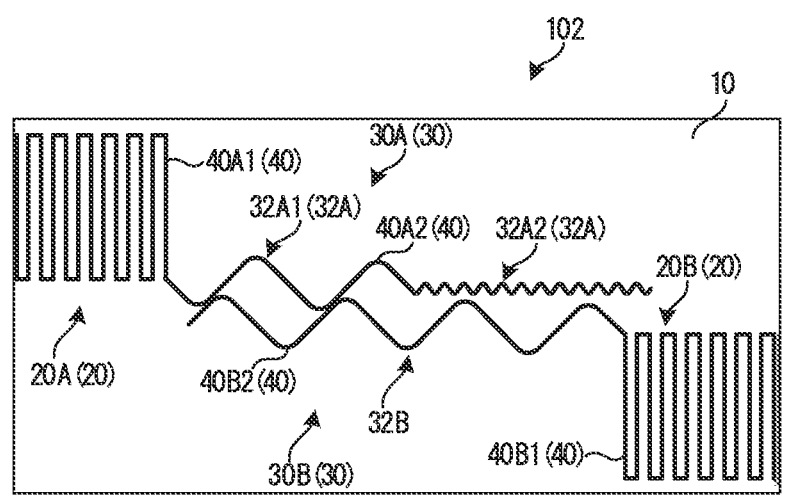
FIG. 11B is a schematic plan view illustrating a first expanded state of the wiring electrode part of the second modification.
Figure 11C:
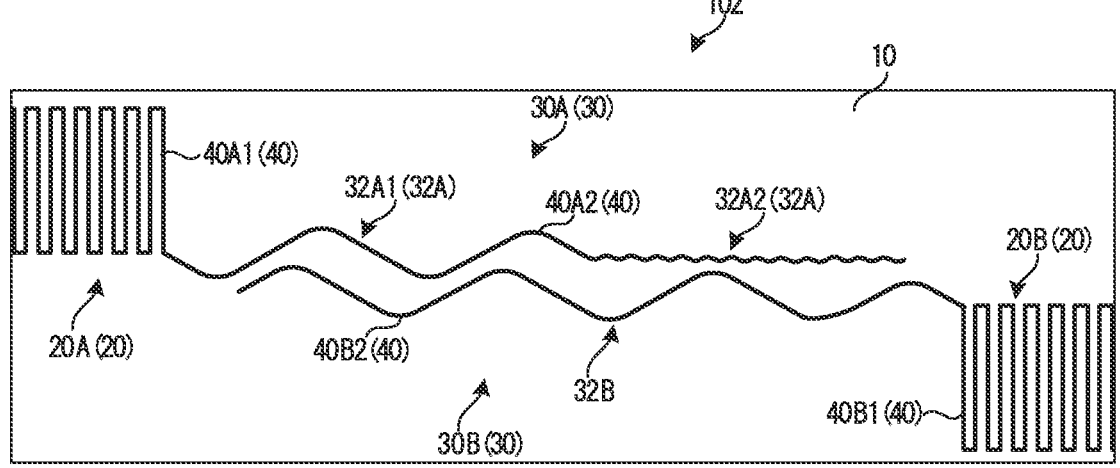
FIG. 11C is a schematic plan view illustrating a second expanded state of the wiring electrode part of the second modification.

When the expanding/contracting portion expands further, the second wave-shaped part 32A2 of the first detection wiring part 30A and the wave-shaped part 32B of the second detection wiring part 30B move apart from each other at the moment when a certain expansion rate is reached (see FIG. 11C).

That is, the second wave-shaped part 32A2 of the first detection wiring part 30A and the wave-shaped part 32B of the second detection wiring part 30B move apart from each other first, and the first wave-shaped part 32A1 of the first detection wiring part 30A and the wave-shaped part 32B of the second detection wiring part 30B move apart from each other subsequently.

When the expanding/contracting portion of the wearable part expands as a result of this motion, the resistance value between the first electrode part 20A and the second electrode part 20B gradually changes. That is, the resistance value gradually increases in proportion to the increase in the contact resistance due to the partial separation between the first detection wiring part 30A and the second detection wiring part 30B. Specifically, in a conductive state between the first electrode part 20A and the second electrode part 20B, the resistance value increases by a certain value, and then the conductive state is changed to a non-conductive state.

The gradual motion of the wearing body can then be detected by detecting the gradual change in resistance value between the first electrode part 20A and the second electrode part 20B that accompanies the expansion.

However, when the expansion of the expanding/contracting portion of the wearable part is released (that is, when the expanding/contracting portion contracts) as a result of the motion of the wearing body, the first wave-shaped part 32A1 of the first detection wiring part 30A and the wave-shaped part 32B of the second detection wiring part 30B, which have been apart from each other, come into contact with each other at the moment when a certain expansion rate is reached (see FIG. 11B).

Further, when the expanding/contracting portion contracts, the second wave-shaped part 32A2 of the first detection wiring part 30A and the wave-shaped part 32B of the second detection wiring part 30B, which have been apart from each other, come into contact with each other at the moment when a certain expansion rate is reached (see FIG. 11A). That is, the resistance value is gradually reduced.

Specifically, the state between the first electrode part 20A and the second electrode part 20B shifts from a non-conduction state to a conduction state, whereupon the resistance value is reduced in the conductive state.

Thus, the gradual motion of the wearing body can be detected by detecting a gradual change in the resistance value between the first electrode part 20A and the second electrode part 20B that accompanies the contraction.

Here, a second modification may have a plurality of regions having mutually different contact lengths in the contact section between the wave-shaped part 32A of the first detection wiring part 30A and the wave-shaped part 32B of the second detection wiring part 30B, according to an intended gradual change in the resistance value between the first electrode part 20A and the second electrode part 20B. The first detection wiring part 30A and/or second detection wiring part 30B may have a plurality of wave-shaped parts having different periods and/or amplitudes.

Note that the gradual change in the resistance value (that is, the gradual increase or decrease) indicates that the resistance value changes in the course of expansion of the expanding/contracting portion of the wearable part, and the resistance value changes again once the resistance value change is complete.

—Third Modification—

Figure 12A:
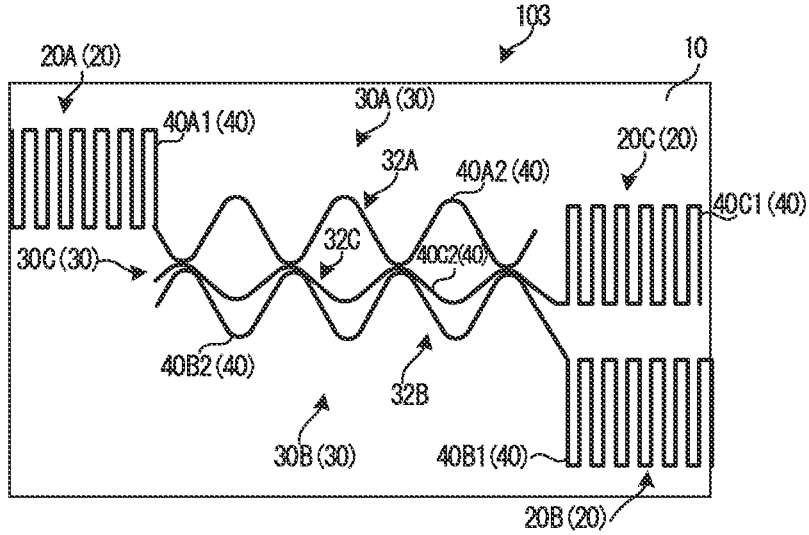
FIG. 12A is a schematic plan view illustrating a wiring electrode part of a third modification.

The wiring electrode part may be, for example, the wiring electrode part 103 illustrated in FIG. 12A. Specifically, as illustrated in FIG. 12A, the wiring electrode part 103 further includes a third electrode part 20C as electrode part 20, and a third detection wiring part 30C as the detection wiring part 30.

The third electrode part 20C includes a conductive linear body 40C 1. The third detection wiring part 30C includes a conductive linear body 40C2 extending from the conductive linear body 40C1 of third electrode part 20C. That is, the third electrode part 20C and the third detection wiring part 30C are configured from at least the same one conductive linear body 40.

The third detection wiring part 30C is electrically connected to the third electrode part 20C.

The third detection wiring part 30C is provided separately from the first detection wiring part 30A and the second detection wiring part 30B so as to be interposed between the first detection wiring part 30A and the second detection wiring part 30B and so as to be in contact with at least a portion of the first detection wiring part 30A and at least a portion of the second detection wiring part 30B in a state before expansion of the expanding/contracting portion (hereinafter, simply referred to as the "expanding/contracting portion of the wearable part") of a wearable part, at which the detection wiring part 30 is provided.

The third detection wiring part 30C has, for example, a wave-shaped part 32C in which the conductive linear body 40C2 is provided in a wave shape.

In the state before expansion of the expanding/contracting portion of the wearable part, the wave-shaped part 32C of the third detection wiring part 30C is in point contact or line contact with the wave-shaped part 32A of the first detection wiring part 30A and the wave-shaped part 32B of the second detection wiring part 30B.

However, the contact length between the wave-shaped part 32C of the third detection wiring part 30C and the wave-shaped part 32A of the first detection wiring part 30A is different from the contact length between the wave-shaped part 32C of the third detection wiring part 30C and the wave-shaped part 32B of the second detection wiring part 30B. The periods and/or amplitudes of the wave-shaped part 32C of the third detection wiring part 30C, the wave-shaped part 32A of the first detection wiring part 30A, and the wave-shaped part 32B of the second detection wiring part 30B are different.

Note that, in this example, the contact length between the wave-shaped part 32C of the third detection wiring part 30C and the wave-shaped part 32A of the first detection wiring part 30A is shorter than the contact length between the wave-shaped part 32C of the third detection wiring part 30C and the wave-shaped part 32B of the second detection wiring part 30B. Here, an example is illustrated in which the wave-shaped part 32C of the third detection wiring part 30C has a smaller amplitude than the wave-shaped part 32A of the first detection wiring part 30A and the wave-shaped part 32B of the second detection wiring part 30B.

Figure 12B:
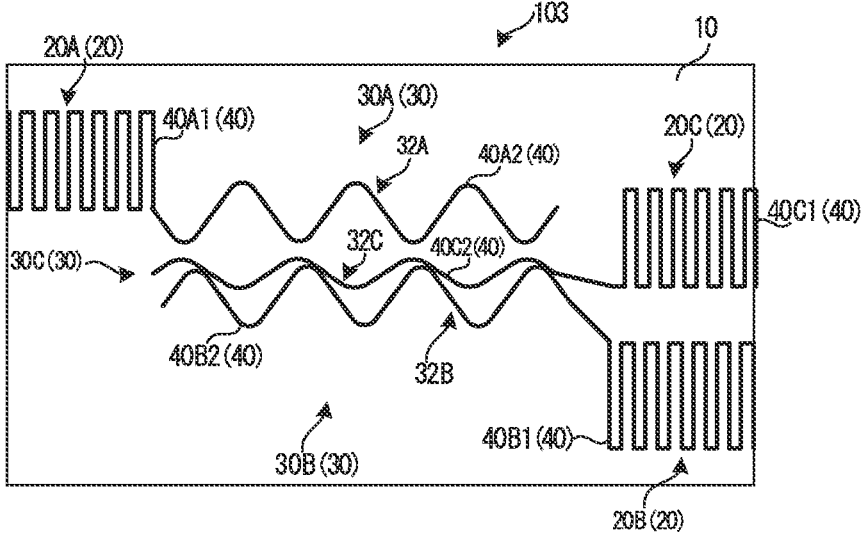
FIG. 12B is a schematic plan view illustrating a first expanded state of the wiring electrode part of the third modification.

When the expanding/contracting portion of the wearable part expands, the first detection wiring part 30A and the third detection wiring part 30C, which have been in contact with each other, move apart from each other at the moment when a certain expansion rate is reached (see FIG. 12B). Specifically, the wave-shaped part 32A of the first detection wiring part 30A and the wave-shaped part 32C of the third detection wiring part 30C move apart from each other.

Figure 12C:
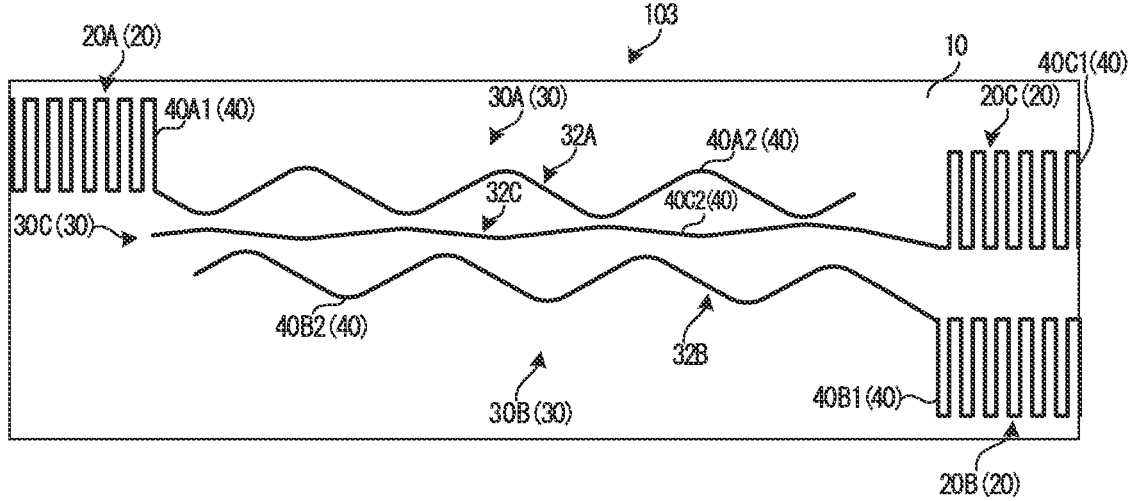
FIG. 12C is a schematic plan view illustrating a second expanded state of the wiring electrode part of the third modification.

When the expanding/contracting portion expands further, the second detection wiring part 30B and the third detection wiring part 30C, which have been in contact with each other, move apart from each other at the moment when a certain expansion rate is reached (see FIG. 12C). Specifically, the wave-shaped part 32B of the second detection wiring part 30B and the wave-shaped part 32C of the third detection wiring part 30C move apart from each other.

That is, the first detection wiring part 30A and the third detection wiring part 30C move apart from each other first, and the second detection wiring part 30B and the third detection wiring part 30C move apart from each other subsequently.

When the expanding/contracting portion of the wearable part expands as a result of this motion, the resistance value between the first electrode part 20A and the third electrode part 20C changes. That is, the resistance value increases. Specifically, the state between the first electrode part 20A and the third electrode part 20C shifts from a conduction state to a non-conduction state.

When the expanding/contracting portion expands further, the resistance value between the second electrode part 20B and the third electrode part 20C changes. That is, the resistance value increases. Specifically, the state between the second electrode part 20B and the third electrode part 20C shifts from a conduction state to a non-conduction state.

The motion of the wearing body can then be detected by detecting a change in the resistance value between the first electrode part 20A and the third electrode part 20C and a change in the resistance value between the second electrode part 20B and the third electrode part 20C that accompany the expansion.

However, when the expansion of the expanding/contracting portion of the wearable part is released (that is, when the expanding/contracting portion contracts) as a result of the motion of the wearing body, the second detection wiring part 30B and third detection wiring part 30C, which have been apart from each other, come into contact with each other at the moment when a certain expansion rate is reached (see FIG. 12B). Specifically, the wave-shaped part 32B of the second detection wiring part 30B and the wave-shaped part 32C of the third detection wiring part 30C come into contact with each other.

When the expanding/contracting portion contracts further, the first detection wiring part 30A and the third detection wiring part 30C, which have been apart from each other, come into contact with each other at the moment when a certain expansion rate is reached (see FIG. 12A). Specifically, the wave-shaped part 32A of the first detection wiring part 30A and the wave-shaped part 32C of the third detection wiring part 30C come into contact with each other.

That is, the second detection wiring part 30B and the third detection wiring part 30C come into contact with each other first, and the first detection wiring part 30A and the third detection wiring part 30C come into contact with each other subsequently.

Thus, the gradual motion of the wearing body can be detected by detecting a change in the resistance value between the first electrode part 20A and the third electrode part 20C and a change in the resistance value between the second electrode part 20B and the third electrode part 20C that accompany the contraction.

Note that, in a third modification, the second detection wiring part 30B and the third detection wiring part 30C may be separated first, and the first detection wiring part 30A and the third detection wiring part 30C may be separated subsequently.

—Fourth Modification—

Figure 13A:
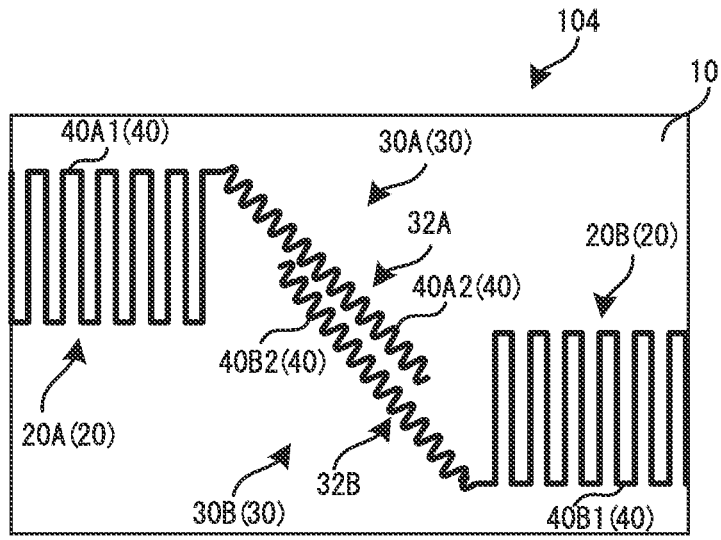
FIG. 13A is a schematic plan view illustrating a wiring electrode part of a fourth modification.

The wiring electrode part may be, for example, the wiring electrode part 104 illustrated in FIG. 13A.

Specifically, as illustrated in FIG. 13A, in the wiring electrode part 104, the first detection wiring part 30A and the second detection wiring part 30B are provided so as to be apart from each other in a state before expansion of the expanding/contracting portion (hereinafter, simply referred to as the "expanding/contracting portion of the wearable part") of the wearable part, at which the detection wiring part 30 is provided. Further, the wave-shaped part 32A of the first detection wiring part 30A and the wave-shaped part 32B of the second detection wiring part 30B are provided so as to face each other at an angle (for example, the angle formed by the direction of extension of each wave-shaped part ranges from 3° to 30°) and so as to be apart from each other.

Figure 13B:
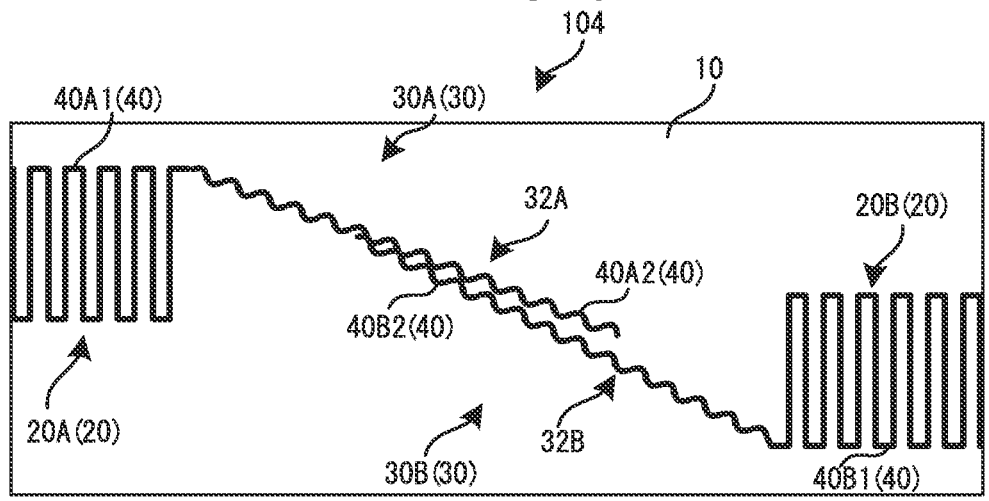
FIG. 13B is a schematic plan view illustrating a first expanded state of the wiring electrode part of the fourth modification.

When the expanding/contracting portion of the wearable part expands as a result of the motion of the wearing body, at least a portion of the first detection wiring part 30A and at least a portion of the second detection wiring part 30B, which have been apart from each other, come into contact with each other at the moment when a certain expansion rate is reached (see FIG. 13B). Specifically, at least a portion of the conductive linear body 40A2 constituting the first detection wiring part 30A and at least a portion of the conductive linear body 40B2 constituting the second detection wiring part 30B come into contact with each other.

More specifically, when the expanding/contracting portion of the wearable part expands, while the periods of the wave-shaped part 32A of the first detection wiring part 30A and the wave-shaped part 32B of the second detection wiring part 30B become long and the amplitudes thereof become small, the tip side (the tip side not connected to the second electrode part 20B) of the wave-shaped part 32B of the second detection wiring part 30B comes into contact with the wave-shaped part 32A of the first detection wiring part 30A.

Figure 13C:
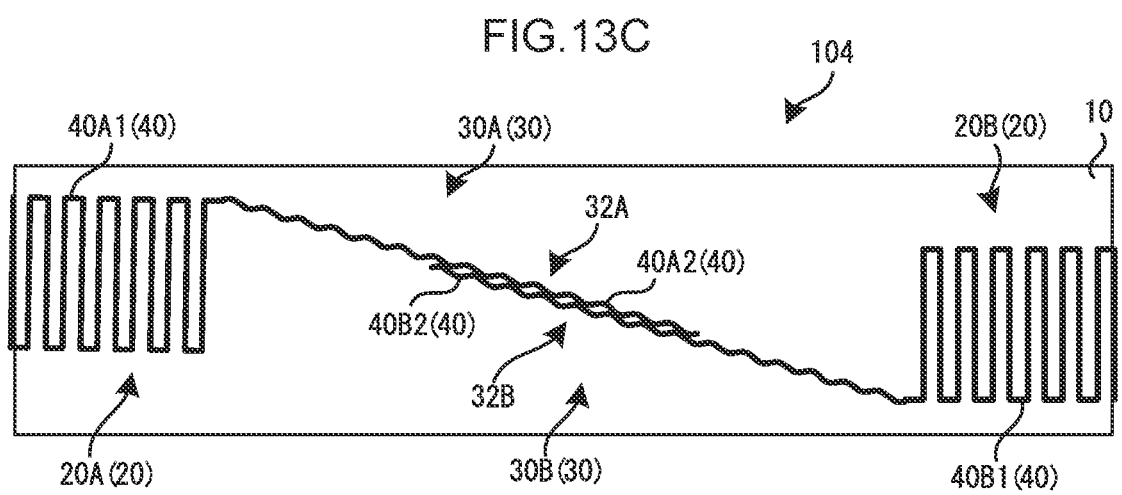
FIG. 13C is a schematic diagram illustrating a second expanded state of the wiring electrode part of the fourth modification.

When the expanding/contracting portion expands further, the contact region increases between the first detection wiring part 30A and the second detection wiring part 30B (see FIG. 13C). Specifically, the contact region increases between the conductive linear body 40A2 constituting the first detection wiring part 30A and the conductive linear body 40B2 constituting the second detection wiring part 30B.

More specifically, when the expanding/contracting portion of the wearable part expands, while the periods of the wave-shaped part 32A of the first detection wiring part 30A and the wave-shaped part 32B of the second detection wiring part 30B become long and the amplitudes thereof becomes small, the contact region increases.

When the expanding/contracting portion of the wearable part expands as a result of this motion, the resistance value between the first electrode part 20A and the second electrode part 20B gradually changes. That is, when the first detection wiring part 30A and the second detection wiring part 30B first come into contact with each other, the state between the first electrode part 20A and the second electrode part 20B shifts from a non-conductive state to a conductive state. Next, when the contact region between the first detection wiring part 30A and the second detection wiring part 30B increases, the contact resistance decreases, and the resistance value between the first electrode part 20A and the second electrode part 20B is gradually reduced.

The gradual motion of the wearing body can then be detected by detecting the gradual change in resistance value between the first electrode part 20A and the second electrode part 20B that accompanies the expansion.

However, when the expansion of the expanding/contracting portion of the wearable part is released (that is, when it contracts) as a result of the motion of the wearing body, the contact region between the first detection wiring part 30A and the second detection wiring part 30B decreases (FIG. 13B). Further, when the expanding/contracting portion contracts, the first wave-shaped part 32A1 of the first detection wiring part 30A and the wave-shaped part 32B of the second detection wiring part 30B, which have been in contact with each other, move apart from each other at the moment when a certain expansion rate is reached (see FIG. 13A). That is, the resistance value gradually increases.

Specifically, the resistance value decreases in a conductive state between the first electrode part 20A and the second electrode part 20B, whereupon the first electrode part and the second electrode part come into a non-conductive state.

Thus, the gradual motion of the wearing body can also be detected by detecting a gradual change in the resistance value between the first electrode part 20A and the second electrode part 20B that accompanies the contraction.

—Fifth Modification—

Figure 14A:
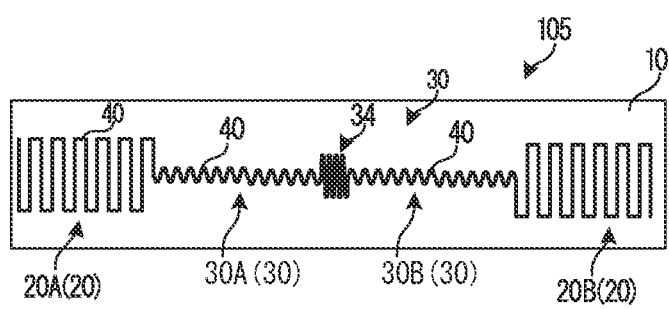
FIG. 14A is a schematic plan view illustrating a wiring electrode part of a fifth modification.

The wiring electrode part may be, for example, the wiring electrode part 105 illustrated in FIG. 14A. Specifically, as illustrated in FIG. 14A, in wiring electrode part 105, the first detection wiring part 30A and the second detection wiring part 30B are integrally provided as the detection wiring part 30. Specifically, for example, the first detection wiring part 30A and the second detection wiring part 30B serving as the detection wiring part 30 are configured from one conductive linear body 40 extending from the conductive linear body 40 constituting the first electrode part 20A and the second electrode part 20B.

That is, in the wiring electrode part 105, the first electrode part 20A and the second electrode part 20B are electrically connected by one detection wiring part 30.

Note that the detection wiring part 30 may be configured from a plurality of conductive linear bodies 40.

Midway along the detection wiring part 30, a contact section 34 is provided in which, in a state before expansion of the expanding/contracting portion (hereinafter, simply referred to as the "expanding/contracting portion of the wearable part") of the wearable part, at which the detection wiring part 30 is provided, the detection wiring part 30 is repeatedly bent or curved at 1800 and at least portions of the detection wiring part 30 between the bent parts or the curved parts are in contact with each other.

That is, midway along the detection wiring part 30, a contact section 34 is provided in which, in a state before expansion of the expanding/contracting portion of the wearable part, the conductive linear body 40 is repeatedly bent or curved at 180° and at least portions of the conductive linear body 40 between the bent parts or the curved parts are in contact with each other.

Figure 14B:
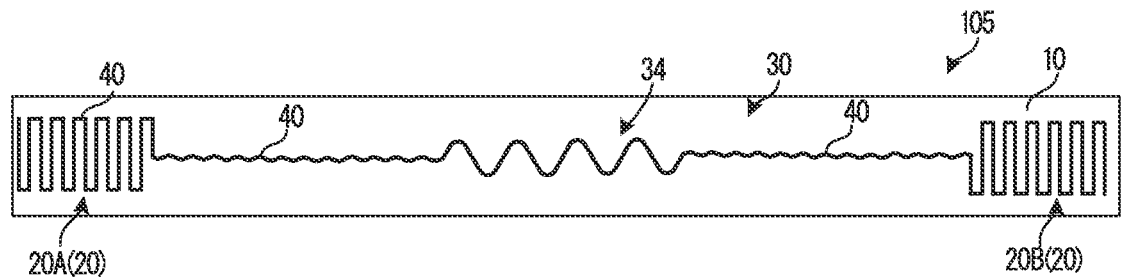
FIG. 14B is a schematic plan view illustrating an expanded state of the wiring electrode part of the fifth modification.

When the expanding/contracting portion of the wearable part expands along the direction of extension of the detection wiring part 30, the portions of the detection wiring part 30, which have been in contact between the bent parts or the curved portions, move apart from each other in the contact section 34 of the detection wiring part 30 (see FIG. 14B). Accordingly, a conduction path of the first electrode part 20A and the second electrode part 20B lengthens.

When the expanding/contracting portion of the wearable part expands as a result of this motion, the resistance value between the first electrode part 20A and the second electrode part 20B changes. That is, the resistance value increases as the conduction path increases.

The motion of the wearing body can then be detected by detecting the change in resistance value between the first electrode part 20A and the second electrode part 20B that accompanies the expansion.

However, when the expansion of the expanding/contracting portion of the wearable part is released (that is, when it contracts) as a result of the motion of the wearing body, the portions of the detection wiring part 30 are repeatedly bent or curved at 180° midway along the detection wiring part 30, and the contact section 34 is formed in which at least portions of the detection wiring part 30 between the bent parts or the curved parts are in contact with each other (see FIG. 14A).

When the expanding/contracting portion of the wearable part contracts as a result of this motion, the resistance value between the first electrode part 20A and the second electrode part 20B changes. That is, the resistance value is reduced as the conduction path decreases.

The motion of the wearing body can also be detected by detecting a change in resistance value between the first electrode part 20A and the second electrode part 20B that accompanies the contraction.

Note that, in a fifth modification, the amount of change in the resistance value between the first electrode part 20A and the second electrode part 20B can be controlled by increasing or decreasing the contact area between the portions of the detection wiring part 30 in the contact section of the detection wiring part 30.

—Sixth Modification—

The electrode wiring part may be, for example, the wiring electrode part 106 illustrated in FIG. 15. That is, an embodiment may be adopted in which the expanding/contracting portion of the glove-shaped wearable part, at which the detection wiring part is provided, is arranged at the surface of the corresponding position of the glove-shaped wearable part.

Specifically, as illustrated in FIG. 15, the wiring electrode part 106 (the electrode part 20, detection wiring part 30, and connection wiring part 50) is provided at the expandable/contractible fabric material 60.

The expandable/contractible fabric material 60 is configured from triple (three layers of) fabric material layers, namely, a front surface fabric material layer 60A constituting a front surface, a back surface fabric material layer 60B constituting a back surface, and an intermediate fabric material layer 60C provided between the front surface fabric material layer 60A and the back surface fabric material layer 60B. Note that the configuration of the expandable/contractible fabric material 60 is similar to the fabric material constituting the glove-shaped wearable part 10.

The electrode part 20 is provided, for example, at the front surface fabric material layer 60A of the expandable/contractible fabric material 60.

The detection wiring part 30 is provided, for example, at the intermediate fabric material layer 60C of the expandable/contractible fabric material 60.

The connection wiring part 50 is provided, for example, at the intermediate fabric material layer 60C of the expandable/contractible fabric material 60.

The expandable/contractible fabric material 60, at which the electrode wiring part 106 is provided, is disposed at the surface of the corresponding position of the glove-shaped wearable part 10 by a well-known fixing means such as sewing or adhesion.

In the sixth modification, because the expandable/contractible fabric material 60, at which the electrode wiring part 106 is provided, is disposed at the surface of the corresponding position of the glove-shaped wearable part 10, the glove-shaped wearable part 10 can be configured from a well-known material such as resin, paper, leather, or the like instead of the fabric material.

—Seventh Modification—

The electrode wiring part may be, for example, the wiring electrode part 107 illustrated in FIG. 16. That is, an embodiment may be adopted in which the expanding/contracting portion of the glove-shaped wearable part, at which the detection wiring part is provided, is arranged at the surface of the corresponding position of the glove-shaped wearable part.

Specifically, as illustrated in FIG. 16, a button electrode (a snap button or the like) serving as the electrode part 20 is arranged at the surface of the corresponding position of the glove-shaped wearable part 10 by using a well-known fixing means such as sewing or adhesion.

The button electrode serving as the electrode part 20 may be connected to the communication module 202 via wiring, or may be directly connected to the communication module 202.

The detection wiring part 30 is provided at the expandable/contractible fabric material 70.

The expandable/contractible fabric material 70 is configured from triple (three layers of) fabric material layers, namely, a front surface fabric material layer 70A constituting the front surface, a back surface fabric material layer 70B constituting a back surface, and an intermediate fabric material layer 70C provided between the front surface fabric material layer 70A and the back surface fabric material layer 70B. Note that the configuration of the expandable/contractible fabric material 70 is similar to the fabric material constituting the glove-shaped wearable part 10.

The expandable/contractible fabric material 70, at which the detection wiring part 30 is provided, is provided at the surface of the glove-shaped wearable part 10.

The connection wiring part 50 is provided so as to connect the electrode part 20 and the detection wiring part 30 at the surface of the glove-shaped wearable part 10. Here, the connection wiring part 50 is covered with a well-known insulating sheet 72 such as a fabric material or a resin material.

Also in the seventh modification, because the electrode wiring part 107 is disposed at the surface of the corresponding position of the glove-shaped wearable part 10, the glove-shaped wearable part 10 can be configured from a well-known material such as resin, paper, leather, or the like, instead of the fabric material.

(Characteristics)

Note that, in order to detect the motion of the wearing body, the expanding/contracting portion (hereinafter, simply referred to as the "expanding/contracting portion of the wearable part") of the wearable part, at which the detection wiring part 30 is provided, may have an expansion rate range in which the resistance value between the first electrode part 20A and the second electrode part 20B changes by 2 times or more or by ½ or less (preferably 10 times or more or ¹⁄₁₀ or less, more preferably 100 times or more or ¹⁄₁₀₀ or less) within a range in which the change in the expansion rate is +5% (see FIGS. 8 to 9). That is, in the expanding/contracting portion of the wearable part, the resistance value between the first electrode part 20A and the second electrode part 20B may change by 2 times or more or by ½ or less while the expansion rate changes by 10% in the course of expansion.

Specifically, when the maximum expansion rate of the expanding/contracting portion of the wearable part is X (where 10≤X), and the expansion rate at a certain point when the expanding/contracting portion of the wearable part is expanded is Y (where 5≤Y≤(X−5)), the expanding/contracting portion may have a region in which the maximum resistance value is 2 times or more or ½ or less (preferably 10 times or more or ¹⁄₁₀ or less, more preferably 100 times or more or ¹⁄₁₀₀ or less) the minimum resistance value within a range of Y−5% to Y+5%.

This resistance value change is calculated using the ratio of resistance values at the moment when an intended expansion rate is reached and at the moment when the expansion rate changes by 10% after this moment.

Note that there may be two or more expansion rate ranges in which the resistance value between the first electrode part 20A and the second electrode part 20B changes by 2 times or more or by ½ or less within a range in which the change in the expansion rate is +5%.

Here, the range, for the ratio between the expansion rate and the maximum expansion rate (expansion rate/maximum expansion rate), in which the resistance value between the first electrode part 20A and the second electrode part 20B changes by 2 times or more or by ½ or less within a range in which the change in the expansion rate is +5%, may be in a range of 0.1 to 0.9 (preferably 0.2 to 0.8). When the ratio is in the aforementioned range, it is possible to efficiently detect the motion of the wearing body while preventing a malfunction.

The change in the resistance value between the first electrode part 20A and the second electrode part 20B that accompanies the expansion/contraction of the expanding/contracting portion of the wearable part is measured as follows.

While measuring the resistance value between the first electrode part 20A and the second electrode part 20B, the expanding/contracting portion of the wearable part is expanded to the maximum expansion at a speed of 1 mm/s, and then contracted at the same speed until returning to the original state. At such time, the resistance value is plotted every 1 second, and a change in the resistance value is measured. Note that the direction of expansion of the expanding/contracting portion of the wearable part is the direction in which a change in resistance value due to expansion/contraction should be detected.

Here, the expansion rate of the expanding/contracting portion of the wearable part is calculated using the formula: ((length in the direction of expansion at the time of expansion)−(length in the direction of expansion before expansion))/(length in the direction of expansion before expansion)×100.

Meanwhile, the maximum expansion rate of the expanding/contracting portion of the wearable part is calculated using the formula: ((length in the direction of expansion at the maximum expansion)−(length in the direction of expansion before expansion))/(length in the direction of expansion before expansion)×100.

Note that the maximum expansion of the expanding/contracting portion of the wearable part is the length at the time when the expanding/contracting portion of the wearable part no longer expands when the expanding/contracting portion is expanded using an appropriate tension. That is, the length in a case in which the expanding/contracting portion of the wearable part is expanded using the tension at which the expansion stops is taken as the maximum expansion of the expanding/contracting portion of the wearable part.

(Shape of Motion Detection Member (Wearable Part Thereof) and the Like)

In the case of the motion detection member according to the present embodiment, the shape of the wearable part is not limited to a glove-shaped shape, rather, various shapes such as a cylindrical shape, a sheet shape, or a belt shape may be used, depending on the purpose.

As a cylindrical wearable part, the shape of a supporter, a wristband, or the like, can be adopted.

As a sheet-shaped wearable part, the shape of a supporter, a wristband, or the like, in which fasteners are provided at both ends for being wound around the wearing body, can be adopted. Note that, in the case of a sheet-shaped wearable part, the embodiment may be such that the sheet-shaped wearable part is bonded to the wearing body using an adhesive.

As a belt-shaped wearable part, the shape of a suspender or the like can be adopted.

Note that the shape of the wearable part is selected according to the location for wearing on the wearing body.

Here, examples of locations for wearing on the wearing body include moving parts (neck, wrist, elbow, shoulder, knee, waist, ankle, foot, and the like) of a human body serving as the wearing body. However, they are not limited thereto.

Thus, the motion detection member according to the present embodiment can be worn at various locations of the wearing body according to the shape of the wearable part.

As a result, for example, the motion of a moving part of the wearing body (such as motion in which a moving part such as an elbow or a knee moves at predetermined angle) and the number of motions thereof can be detected. Furthermore, the size of the arm and the waist can be measured. Here, motion can also be detected using a plurality of measurements (for example, the motion of a person can be predicted and detected by measuring, in combination, the neck, the wrist, the elbow, the shoulder, the knee, the waist, the ankle, the foot, and the like).

OTHERS

The motion detection member according to the present embodiment may also be provided with a well-known sensor other than the detection wiring part 30 (for example, a contact-type sensor or the like). By providing a well-known sensor other than the detection wiring part 30, superior motion detection is possible.

The disclosure of Japanese Patent Application No. 20204053218, filed on Mar. 24, 2020, is incorporated in the present specification by reference in its entirety. All documents, patent applications, and technical standards disclosed in the present specification are incorporated herein by reference to the same extent as if the individual documents, patent applications, and technical standards were specifically and individually marked as being incorporated by reference.

The invention claimed is:

1. A motion detection member for detecting motion of a wearing body, the motion detection member comprising:
a wearable part that is to be worn on the wearing body, the wearable part including an expanding/contracting portion that is configured from an expandable/contractible fabric material that expands/contracts as a result of the motion of the wearing body; and
a wiring electrode part including: a wiring part provided at at least a portion of the expanding/contracting portion of the wearable part, the wiring part including a first wiring part including a conductive linear body and a second wiring part including a conductive linear body; and an electrode part including a first electrode part electrically connected to the first wiring part and a second electrode part electrically connected to the second wiring part,
wherein, when the expanding/contracting portion of the wearable part, at which the wiring part is provided, expands/contracts as a result of the motion of the wearing body, a contact state between the first wiring part and the second wiring part changes, so that a resistance value between the first electrode part and the second electrode part changes.

2. The motion detection member according to claim 1, wherein:
the first wiring part and the second wiring part are separately provided;
in a case in which the first wiring part and the second wiring part are provided so that at least a portion of the first wiring part and at least a portion of the second wiring part are in contact with each other before expansion of the expanding/contracting portion of the wearable part, at which the wiring part is provided, when the expanding/contracting portion of the wearable part, at which the wiring part is provided, expands as a result of the motion of the wearing body, the first wiring part and the second wiring part move apart from each other; and in a case in which the first wiring part and the second wiring part are provided so as to be apart from each other before expansion of the expanding/contracting portion of the wearable part, at which the wiring part is provided, when the expanding/contracting portion of the wearable part, at which the wiring part is provided, expands as a result of the motion of the wearing body, at least a portion of the first wiring part and at least a portion of the second wiring part come into contact with each other.

3. The motion detection member according to claim 1, wherein:

the first wiring part and the second wiring part are separately provided;

in a case in which the first wiring part and the second wiring part are provided so that at least a portion of the first wiring part and at least a portion of the second wiring part are in contact with each other before expansion of the expanding/contracting portion of the wearable part, at which the wiring part is provided, when the expanding/contracting portion of the wearable part, at which the wiring part is provided, expands as a result of the motion of the wearing body, a contact region between the first wiring part and the second wiring part gradually decreases; and in a case in which the first wiring part and the second wiring part are provided so as to be apart from each other before expansion of the expanding/contracting portion of the wearable part, at which the wiring part is provided, when the expanding/contracting portion of the wearable part, at which the wiring part is provided, expands as a result of the motion of the wearing body, the contact region between the first wiring part and the second wiring part gradually increases.

4. The motion detection member according to claim 1, wherein:

the first wiring part and the second wiring part are integrally provided; and when the expanding/contracting portion of the wearable part, at which the wiring part is provided, expands as a result of the motion of the wearing body, a conduction path of the first wiring part and the second wiring part lengthens.

5. The motion detection member according to claim 1, having an expansion rate range such that, when the expanding/contracting portion of the wearable part, at which the wiring part is provided, is expanded to a maximum expansion rate, the resistance value between the first electrode part and the second electrode part changes by two times or more or by ½ or less within a range of an expansion rate change of ±5%.

6. The motion detection member according to claim 1, wherein the resistance value between the first electrode part and the second electrode part gradually changes according to an expansion rate of the expanding/contracting portion of the wearable part, at which the wiring part is provided.

7. The motion detection member according to claim 1, wherein, when the expanding/contracting portion of the wearable part, at which the wiring part is provided, expands, a state between the first electrode part and the second electrode part shifts from a conduction state to a non-conduction state or from a non-conduction state to a conduction state.

8. The motion detection member according to claim 1, wherein a portion of the conductive linear body in at least one of the first electrode part or the second electrode part is bound by a yarn of the expandable/contractible fabric material of the expanding/contracting portion of the wearable part.

9. The motion detection member according to claim 8, wherein the conductive linear body in at least one of the first electrode part or the second electrode part is woven into, knitted into, or embroidered onto the expandable/contractible fabric material of the expanding/contracting portion of the wearable part.

10. The motion detection member according to claim 1, wherein a portion of the conductive linear body in at least one of the first wiring part or the second wiring part is bound by a yarn of the expandable/contractible fabric material of the expanding/contracting portion of the wearable part.

11. The motion detection member according to claim 10, wherein the conductive linear body in at least one of the first wiring part or the second wiring part is woven into, knitted into, or embroidered onto the expandable/contractible fabric material of the expanding/contracting portion of the wearable part.

12. The motion detection member according to claim 1, wherein at least one of the first wiring part or the second wiring part is provided inside the expandable/contractible fabric material of the expanding/contracting portion of the wearable part.

13. The motion detection member according to claim 1, wherein the conductive linear body included in at least one of the first electrode part, the second electrode part, the first wiring part, or the second wiring part is a conductive linear body that includes a carbon nanotube yarn.

14. The motion detection member according to claim 1, wherein the wearable part is a glove-shaped wearable part that is to be worn on a hand of a human body serving as the wearing body.

15. The motion detection member according to claim 14, wherein the expanding/contracting portion, at which the wiring part is provided, faces at least one of a proximal interphalangeal joint or a metacarpophalangeal joint of a finger of the hand.

16. The motion detection member according to claim 1, wherein the wearable part is a cylindrical, sheet-shaped, or belt-shaped wearable part.

17. The motion detection member according to claim 16, wherein the cylindrical, sheet-shaped, or belt-shape wearable part is a wearable part that is to be worn on a moving part of a human body serving as the wearing body.

18. The motion detection member according to claim 1, wherein the expanding/contracting portion of the wearable part, at which the wiring part is provided, is provided at a surface of the wearable part.

* * * * *